(12) United States Patent
Bryson et al.

(10) Patent No.: US 6,500,783 B1
(45) Date of Patent: Dec. 31, 2002

(54) PROCESS AND COMPOSITIONS PROMOTING BIOLOGICAL EFFECTIVENESS OF EXOGENOUS CHEMICAL SUBSTANCES IN PLANTS

(75) Inventors: Nathan J. Bryson, Millery; Olivier Soula, Lyon; Alain J. L. Lemercier, St. Bonnet de Mûre; Rémi Meyrueix, Lyon; Gérard G. Soula, Meyzieux, all of (FR)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/451,283

(22) Filed: Nov. 30, 1999

Related U.S. Application Data

(60) Provisional application No. 60/110,212, filed on Nov. 30, 1998.

(51) Int. Cl.⁷ .................................................. A01N 25/30
(52) U.S. Cl. ...................................... 504/206; 504/362
(58) Field of Search ................................ 504/206, 362

(56) References Cited

U.S. PATENT DOCUMENTS

| | | | |
|---|---|---|---|
| 3,799,758 A | 3/1974 | Franz | 71/86 |
| 3,853,530 A | 12/1974 | Franz | 71/76 |
| 4,140,513 A | 2/1979 | Prill | 71/86 |
| 4,315,765 A | 2/1982 | Large | 71/87 |
| 4,405,531 A | 9/1983 | Franz | 260/501.12 |
| 4,431,594 A | 2/1984 | Broadhurst et al. | 260/502.5 F |
| 4,481,026 A | 11/1984 | Prisbylla | 71/86 |
| 4,507,250 A | 3/1985 | Bakel | 260/502.5 F |
| 4,693,742 A | 9/1987 | Patterson | 71/86 |
| 4,853,026 A | 8/1989 | Frisch et al. | 71/86 |
| 5,248,086 A | 9/1993 | Waldrum et al. | 239/10 |
| 5,389,680 A | 2/1995 | Ruminski | 514/563 |
| 5,464,807 A | 11/1995 | Claude et al. | 504/206 |
| 5,538,937 A | 7/1996 | Hasebe et al. | 504/116 |
| 5,563,111 A | 10/1996 | Hioki et al. | 504/116 |
| 5,668,085 A | 9/1997 | Forbes et al. | 504/206 |
| 5,750,468 A | 5/1998 | Wright et al. | 504/206 |
| 6,133,199 A | * 10/2000 | Soula et al. | 504/206 |

FOREIGN PATENT DOCUMENTS

| | | | |
|---|---|---|---|
| EP | 0 124 351 | 11/1984 | C07F/9/38 |
| EP | 0 148 169 | 7/1985 | B01J/13/02 |
| EP | 0 202 027 A1 | 11/1986 | A01N/57/20 |
| EP | 0 360 181 A2 | 3/1990 | C07F/9/30 |
| EP | 0 379 852 | 8/1990 | A01N/57/20 |
| EP | 0 485 207 | 5/1992 | A01N/25/04 |
| FR | 2 489 332 | 3/1982 | C07F/9/08 |
| FR | 2 766 669 | 2/1999 | A01N/57/02 |
| WO | 83/03608 | 10/1983 | C07F/9/28 |
| WO | WO 95/17817 | 7/1995 | |
| WO | 96/32839 | 10/1996 | |
| WO | WO 97/05779 | 2/1997 | A01N/25/30 |
| WO | 98/06259 | 2/1998 | A01N/25/00 |
| WO | WO 98/53680 | 12/1998 | A01N/25/04 |
| WO | WO 99/05914 | 2/1999 | A01N/57/20 |

* cited by examiner

*Primary Examiner*—S. Mark Clardy
(74) *Attorney, Agent, or Firm*—Senniger, Powers, Leavitt & Roedel; Joseph A. Schaper

(57) ABSTRACT

A plant treatment composition for application of an anionic exogenous chemical substance such as glyphosate to foliage of a plant is provided. The composition comprises, in addition to the exogenous chemical substance, one or more amine compound(s) each having a number n of protonatable amino groups, n being at least 1, and having the formula (I)

$$R-NR-((CH_2)_p-CHR^4-NR)_q-R \qquad (I)$$

wherein q is an integer of 0 to 9, each p is independently an integer of 1 to 5, each $R^4$ group is independently hydrogen or a $C_{1-5}$ alkyl group, and R groups are independently selected from hydrogen, $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide, ester, thioester and amide linkages, and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted. The exogenous chemical substance and amine compound(s) of formula (I) are dissolved or dispersed in an agronomically acceptable liquid carrier, preferably water. Also provided are a liquid concentrate composition which, upon dilution with water, forms a plant treatment composition, and a process for making such a liquid concentrate composition. Plant treatment compositions of the invention are useful for eliciting a biological activity, for example herbicidal activity, in a plant.

49 Claims, No Drawings

PROCESS AND COMPOSITIONS PROMOTING BIOLOGICAL EFFECTIVENESS OF EXOGENOUS CHEMICAL SUBSTANCES IN PLANTS

CROSS-REFERENCE TO RELATED APPLICATIONS

This application claims the benefit of U.S. Provisional Application No. 60/110,212 filed Nov. 30, 1998.

FIELD OF THE INVENTION

The field of the present invention is that of exogenous chemical substances applied to foliage of plants, and relates particularly to a process and to compositions applied by that process for promoting biological effectiveness of such exogenous chemical substances.

The term "exogenous chemical substance" as used herein means a chemical substance, whether naturally or synthetically obtained, which is applied to a plant to result in expressing a desired biological activity. The term "biological activity" as used herein means elicitation of a stimulatory, inhibitory, regulatory, therapeutic, toxic or lethal response in the plant or in a pathogen, parasite or feeding organism present in or on the plant. Examples of exogenous chemical substances include, but are not limited to, chemical pesticides (such as herbicides, algicides, fungicides, bactericides, viricides, insecticides, miticides, nematicides and molluscicides), plant growth regulators, fertilizers and nutrients, gametocides, defoliants, desiccants, mixtures thereof and the like.

The term "biological effectiveness" is used herein to denote the degree to which a desired biological activity is expressed upon application of an exogenous chemical substance to foliage of a plant, or alternatively to denote the dosage or rate of application of the exogenous chemical substance that results in the desired biological activity being expressed to a given degree. For example, where the exogenous chemical substance is a herbicide, biological effectiveness can be measured by the degree of inhibition of plant growth resulting from application of a particular rate of the herbicide, or by the application rate of the herbicide required to cause a particular degree of inhibition, e.g., 50% or 85% inhibition. Thus increased or enhanced biological effectiveness of a herbicide can be exhibited for example as an increased level of plant growth inhibition at a given rate of the herbicide, or as a reduction in the minimum rate of the herbicide giving a certain threshold level of plant growth inhibition.

BACKGROUND OF THE INVENTION

For many purposes in agriculture and related endeavors it is desired to treat plants with exogenous chemical substances of various kinds. Many exogenous chemical substances are applied to foliage (i.e., leaves and other non-woody above-ground parts) of a plant, and have a site of action in the plant either close to or remote from the locus of application. Such substances are referred to herein as foliar-applied exogenous chemical substances.

Typically, when an exogenous chemical substance is applied to foliage by plant treatment processes known in the art, only a small portion of the amount applied reaches sites of action in the plant where a desired biological activity of the exogenous chemical substance can be usefully expressed. It is therefore a major desideratum in agriculture and related endeavors to enhance the efficiency of delivery of foliar-applied exogenous chemical substances to their sites of action in plants, and thereby to enhance the biological effectiveness of the exogenous chemical substance for the purpose for which the exogenous chemical substance is used.

Application to foliage of an exogenous chemical substance by processes known in the art does not universally result in inefficient delivery to sites of action. In some situations such processes provide excellent biological effectiveness, even at a low use rate of the exogenous chemical substance. In other situations the same processes, using the same rate of the exogenous chemical substance, provide inadequate biological effectiveness. Thus, these processes are inconsistent in the result they provide, or they cannot be relied upon to provide the desired result.

A problem is that it is seldom possible to identify in advance those situations where good biological effectiveness will be obtained, partly because so many factors influence efficiency of delivery. These factors include weather (temperature, relative humidity, daylength, cloudiness, precipitation, wind, etc.) preceding, during and following application, soil conditions (fertility, aeration, etc.), plant growth stage, health and physiological status, equipment-related inaccuracies in application, and other factors. Therefore, to help ensure reliable or consistent biological effectiveness of a foliar-applied exogenous chemical substance, the user typically applies the substance at a higher rate than truly necessary in the majority of situations.

Variability in biological effectiveness in field conditions is an especially troublesome problem in the case of exogenous chemical substances that are acids, and are typically formulated as water-soluble salts in which the exogenous chemical substance is present in an anionic form. Sometimes by converting such acid substances to esters, this variability can be moderated; however, in many cases esters show reduced biological effectiveness, for example due to inadequate conversion back to the parent acid once inside the treated plant. There remains a strong need for enhanced biological effectiveness, and enhanced reliability of biological effectiveness, of foliar-applied exogenous chemical substances, particularly anionic exogenous chemical substances.

The term "anionic exogenous chemical substance" as used herein means an exogenous chemical substance whose molecular structure includes one or more acid, or proton-donating, sites, and is therefore capable of forming an anion in the presence of a proton acceptor. The term therefore embraces substances that are zwitterionic. In describing an exogenous chemical substance as "anionic" herein, it is not implied that the exogenous chemical substance is necessarily in anionic form or that it is dissociated.

Benefits of a process providing greater reliability of biological effectiveness include an ability to reduce rates of application of exogenous chemical substances without sacrificing consistency of biological effectiveness. Pressures felt by the agricultural industry to reduce pesticide, particularly herbicide, usage are well evidenced by symposia on the subject, such as that held in 1993 by the Weed Science Society of America and documented in *Weed Technology* 8, 331–386 (1994). Reduced use rates bring rewards not only environmentally but also economically, as the cost per unit area treated decreases.

Foliar-applied exogenous chemical substances have frequently been applied together with amphiphilic materials, particularly amphiphilic surface-active agents, otherwise known as surfactants. Surfactants can influence biological effectiveness of a foliar-applied exogenous chemical substance in numerous ways.

When a dilute aqueous composition of an exogenous chemical substance is applied to foliage by conventional hydraulic spraying, the presence of surfactant in the dilute aqueous composition can alter the size distribution of the spray droplets, typically increasing the percentage of spray volume in the form of small droplets and reducing the percentage of spray volume in the form of large droplets. As smaller droplets have lower momentum than larger droplets, these smaller droplets are less likely to rebound from a foliar surface and consequently are more likely to be retained on that surface. Spray retention can also be facilitated by adhesion between surfactant molecules in a spray droplet and the foliar surface, which in most plants is waxy and hydrophobic. This adhesion reduces not only rebound but also run-off of spray droplets from the foliar surface. Surfactants also tend to increase the area of contact between a spray droplet and a foliar surface, and in many cases enhance penetration of an exogenous chemical substance from the droplet into and through cuticles of leaves to reach internal leaf tissues.

Through these and perhaps other effects, amphiphilic materials including surfactants have long been known to increase the biological effectiveness of exogenous chemical substances. It is therefore commonplace for one or more surfactants to be included in commercial formulations of foliar-applied exogenous chemical substances, even in formulations that do not require the presence of surfactants for acceptable physical stability or handling properties, for example as emulsifying or suspending agents or dispersants.

One of the most extensively studied of foliar-applied anionic exogenous chemical substances, from the point of view of the role of surfactants in enhancing biological effectiveness, is the herbicide glyphosate. As well as being a phytotoxic agent, glyphosate has been used as a plant growth regulator.

Glyphosate (N-phosphonomethylglycine) in its strict sense is an acid compound, but the word "glyphosate" is herein used in a less restrictive sense, except where the context dictates otherwise, to encompass not only glyphosate acid but also salts, adducts and esters thereof, and compounds which are converted to glyphosate in plant tissues or which otherwise provide glyphosate ions. In most commercial formulations of glyphosate, the glyphosate is present as a water-soluble salt. In this respect, glyphosate is typical of most exogenous chemical substances that are acids or that form anions.

Herbicidal salts of glyphosate are disclosed, for example, in U.S. Pat. No. 3,799,758 to Franz, U.S. Pat. No. 3,853,530 to Franz, U.S. Pat. No. 4,140,513 to Prill, U.S. Pat. No. 4,315,765 to Large, U.S. Pat. No. 4,405,531 to Franz, U.S. Pat. No. 4,481,026 to Prisbylla and U.S. Pat. No. 4,507,250 to Bakel. In most of the salts disclosed, the counterion to glyphosate anion is a relatively low molecular weight, non-amphiphilic cation. Typical of such salts are alkali metal, for example sodium and potassium, salts; ammonium salt; and numerous salts having an ammonium, sulfonium or sulfoxonium cation substituted with 1–3 organic groups containing in total 1–6 carbon atoms, for example dimethylammonium, isopropylammonium, ethanolammonium and trimethylsulfonium salts.

Commercial formulations of glyphosate salts include, for example, Roundup® brand, Accord® brand, Roundup® Ultra brand and Roundup® Xtra brand herbicides of Monsanto Company, which contain the isopropylammonium salt, Roundup® Dry brand and Rival® brand herbicides of Monsanto Company, which contain the ammonium salt, Roundup® Geoforce brand herbicide of Monsanto Company, which contains the sodium salt, and Touchdown® brand herbicide of Zeneca, which contains the trimethylsulfonium salt.

Salts of glyphosate with higher molecular weight, amphiphilic cations have also been disclosed. Such amphiphilic cations include those having a hydrophilic moiety such as an ammonium, ethanolammonium, polyoxyethylene ammonium, or sulfonium group, and a hydrophobic moiety comprising 1 to 4 hydrocarbyl groups having in total more than 6 carbon atoms. For example, above-cited U.S. Pat. No. 4,405,531, the disclosure of which is incorporated herein by reference, discloses a wide range of primary, secondary and tertiary ammonium salts of glyphosate wherein the cation is amphiphilic as defined immediately above and has a molecular weight of less than about 300. Examples include $C_{6-18}$ alkylammonium cations. International Publication No. WO 83/03608, European Patent Application No. 0 124 351 and U.S. Pat. No. 4,431,594 disclose various quaternary ammonium salts of glyphosate wherein the cation is amphiphilic. U.S. Pat. No. 5,668,085 discloses salts of glyphosate with amphiphilic cations derived from polyoxyethylene tertiary $C_{8-22}$ alkylamine surfactants, a specifically disclosed example being the N-cocoalkyl-N,N-diethanolammonium salt of glyphosate where "cocoalkyl" refers to a mixture of predominantly $C_{12}$ and $C_{14}$ alkyl chains, derived from coconut oil.

Glyphosate as a herbicide has many advantages, particularly environmental advantages including biodegradability and low ecotoxicity. However, studies have shown that even the most biologically effective formulations of glyphosate presently in use do not deliver glyphosate efficiently to sites in the plant where the glyphosate exerts its phytotoxic effect. Typically, only a small fraction of the applied herbicide arrives at such sites.

The small fraction of applied glyphosate which reaches sites of phytotoxic action is related to the fact that the glyphosate must go through several barriers. Among these, one of the most important is believed to be the lipophilic cuticle on the foliar surface to which the glyphosate is applied. It has therefore been theorized that it would be desirable to place the glyphosate into an amphiphilic medium which would provide greater compatibility between the lipophilic cuticle and the hydrophilic glyphosate, and thereby facilitate penetration of glyphosate into and through the cuticle. Similar thinking has been applied to other exogenous chemical substances, particularly those typically formulated as water-soluble salts.

That the concept of an amphiphilic medium as an aid to cuticular penetration and thereby enhanced biological effectiveness, for example of glyphosate, has validity is demonstrated by many studies in which foliar uptake or effectiveness has been enhanced by surfactants. An extensive study by Wyrill & Burnside, *Weed Science* 25, 275–287, 1977 led to a conclusion that "an effective surfactant is a critical component of any glyphosate spray mixture", but noted great variation among surfactant types in the degree of enhancement of herbicidal effectiveness afforded. In general, cationic surfactants gave greater enhancement than nonionic surfactants.

Data are reported in International Publication No. WO 98/06259 for a wide range of cationic, nonionic, anionic and amphoteric surfactants applied either in mixture with, or in sequence following, a glyphosate composition.

International Publication No. WO 96/32839 discloses certain polyoxyethylene etheramine surfactants said to be useful in glyphosate herbicide compositions. These surfactants have a chemical structure wherein the nitrogen atom of an amine group has attached thereto (i) a hydrocarbyl chain interrupted by 1–10 ether linkages and terminated by an uninterrupted hydrocarbyl segment having at least 6 carbon atoms, and (ii) two polyoxyethylene chains having no terminal hydrocarbyl segment.

Another approach to providing an amphiphilic medium has been to apply glyphosate together with a lipophilic agent, such as an oil, in the form of a water-in-oil emulsion or microemulsion. Such emulsions or microemulsions are disclosed in European Patent Application No. 0 379 852, U.S. Pat. Nos. 4,853,026 and 5,248,086. A disadvantage of such microemulsions is that, when provided as concentrate compositions, they are subject to the phenomenon of breaking of the emulsion upon dilution with water to concentrations suitable for application, for example, 5 grams of glyphosate, expressed as acid equivalent, per liter (g a.e./l). In other words, water-in-oil microemulsions tend not to withstand dilution in water. The failure of such microemulsions to provide improved cuticular penetration is perhaps related to this inability to withstand dilution.

Oil-in-water macroemulsion formulations of glyphosate have also been investigated. In these macroemulsions, the majority of the glyphosate is present in the continuous aqueous phase, as shown, for example, in European Patent Application No. 0 485 207. Such macroemulsions, in which the glyphosate and the lipophilic component are segregated, do not therefore provide glyphosate in an amphiphilic form, and have generally not enhanced delivery of glyphosate to its sites of phytotoxic action in the plant.

A different approach, illustrated in European Patent Specification No. 0 148 169, is to encapsulate a water-soluble herbicide such as glyphosate in a polymeric shell by interfacial polycondensation. In this technique, a water-in-oil emulsion having a lipophilic emulsifier based on alkylated polyvinylpyrrolidone is used. Polymerization to form the shell, by reaction of comonomers, occurs at the oil-water interface of the emulsion containing the herbicide, resulting in formation of a shell that encapsulates the herbicide.

All of the approaches summarized above, including formulating an anionic exogenous chemical substance as an amphiphilic salt, have met with limited success in overcoming the barriers to delivery of the exogenous chemical substance to its sites of biological action in the plant. It is an objective, therefore, of the present invention to provide a new composition or formulation of an exogenous chemical substance, in particular an anionic exogenous chemical substance, that can provide superior biological effectiveness when applied to foliage of a plant.

Another objective is to provide a composition or formulation of an exogenous chemical substance, in particular an anionic exogenous chemical substance, that is economical and simple to make.

Another objective of the invention, particularly as it applies to the herbicide glyphosate, is to provide a composition or formulation that meets the previously stated objectives while permitting maintenance of the non-ecotoxic and biodegradable character of glyphosate.

Another objective of the invention is to provide a composition or formulation of an exogenous chemical substance, particularly an anionic exogenous chemical substance, that can be applied in a dilute aqueous medium and does not lose its beneficial properties at high rates of dilution.

Another objective of the invention is to provide an aqueous composition or formulation of an anionic exogenous chemical substance in the form of an amphiphilic salt that is physically stable, even at high concentration, without the need for additional stabilizing agents such as dispersants or emulsifying agents.

Another objective of the invention is to provide a convenient and economical method for the preparation of a composition or formulation that meets the objectives stated above.

Another objective of the invention is to provide a practical and effective alternative to previously known compositions of an anionic exogenous chemical substance such as glyphosate herbicide.

One or more of the above objectives have been satisfied through design of a new approach for promoting transport of an anionic exogenous chemical substance into plants via foliage, and thereby promoting biological effectiveness of the exogenous chemical substance. This approach is set out more fully below.

SUMMARY OF THE INVENTION

A plant treatment composition for application to foliage of a plant to elicit a biological response is now provided, comprising an anionic exogenous chemical substance and one or more amine compound(s) each having a number n of protonatable amino groups, n being at least 1, and having the formula (I)

$$R\text{—}NR\text{—}((CH_2)_p\text{—}CHR^4\text{—}NR)_q\text{—}R \qquad (I)$$

wherein q is an integer of 0 to 9, each p is independently an integer of 1 to 5, each $R^4$ group is independently hydrogen or a $C_{1-5}$ alkyl group, and R groups are independently selected from hydrogen, $C_{1-5}$ hydrocarbyl groups and linear or branched, saturated or unsaturated $C_{6-22}$ hydrocarbyl or acyl chains that are each (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide, ester, thioester and amide linkages and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted.

The exogenous chemical substance is present in the plant treatment composition in an amount sufficient to elicit the biological response when the composition is applied to the foliage of the plant at a rate from about 10 to about 1000 liters per hectare (l/ha). The amine compound(s) of formula (I) are present in the composition in an amount such that the mole ratio of protonatable amino groups in such compound (s) to the exogenous chemical substance is about 0.05:1 to about 2:1, preferably about 0.1:1 to about 1:1. The exogenous chemical substance and amine compound(s) of formula (I) are dissolved or dispersed in an agronomically acceptable liquid carrier, preferably water.

In a first embodiment of the invention, the composition comprises an aqueous application medium, in which supramolecular aggregates are colloidally dispersed. The supramolecular aggregates comprise one or more amphiphilic salt(s) having anions of the anionic exogenous chemical substance and cations derived by protonation of the amine compound(s) of formula (I), such amphiphilic salt(s), including any fraction thereof existing outside the supramolecular aggregates, comprising about 5 to 100 mole percent, preferably about 10 to 100 mole percent, of the exogenous chemical substance present in the composition as a whole. The balance to 100 mole percent of the exogenous chemical substance is present in the form of one or more salt(s) having cations contributed by base(s) other than an amine compound of formula (I), and/or in acid form, it being preferred that not more than about 10 mole percent of the exogenous chemical substance is in acid form.

Reference herein to molar amounts (e.g., mole percent) present of an anionic exogenous chemical substance in salt form is based upon a presumption that unreacted acid and base do not coexist in the composition but does not imply that such presumption is necessarily correct or valid. Indeed it is believed that the acid-base neutralization process providing amphiphilic salt(s) as defined above is complex and can result in the coexistence of unreacted acid and base. Where the number of protonatable groups n in the amine compound is greater than 1, each such protonatable group is considered capable of neutralizing a molecule of the exogenous chemical substance.

In this first embodiment, the cations contributed by base (s) other than an amine compound of formula (I), if present, are preferably selected from alkali metal cations, ammonium cations, organic ammonium or sulfonium cations having in total 1–6 carbon atoms, and trialkylammonium cations wherein alkyl groups each have 4–6 carbon atoms.

In a second embodiment of the invention, the composition comprises an aqueous application medium, in which are dissolved or dispersed the anionic exogenous chemical substance and the amine compound(s) of formula (I), wherein supramolecular aggregates as defined herein are optionally present but wherein substantially no amphiphilic salt of the exogenous chemical substance is present in such supramolecular aggregates. Preferably in this second embodiment the exogenous chemical substance is present as a water-soluble salt (herein referred to as a "low molecular weight salt") wherein the cationic counterion has a molecular weight lower than about 100, and each of the amine compound(s) of formula (I) is present as a salt formed with an acid that is not an exogenous chemical substance as defined herein. More preferably the cationic counterion of the exogenous chemical substance salt is a monovalent cation selected from alkali metal cations, ammonium cations, and organic ammonium and sulfonium cations having in total 1–3 carbon atoms.

The requirement in this second embodiment that "substantially no amphiphilic salt of the exogenous chemical substance is present" in supramolecular aggregates is satisfied where, in a composition of the invention, (1) substantially no supramolecular aggregates exist or can be identified by techniques disclosed herein; or (2) supramolecular aggregates are identifiably present but are determined by techniques known in the art to contain substantially none of the exogenous chemical substance; or (3) supramolecular aggregates are identifiably present but substantially all of the exogenous chemical substance is determined by techniques known in the art to be present in the aqueous medium.

In a third embodiment of the invention, the composition comprises an aqueous application medium, in which are dissolved or dispersed the anionic exogenous chemical substance and the amine compound(s) of formula (I). This third embodiment is independent of the existence of an association, ionic or otherwise, between the anionic exogenous chemical substance and the amine compound(s), whether in supramolecular aggregates or elsewhere. Preferably in this third embodiment the anionic exogenous chemical substance is accompanied by one or more species of monovalent cationic counterion each having a molecular weight lower than about 100, in a total cationic/anionic mole ratio of about 0.5:1 to about 1.8:1. More preferably the cationic counterions are selected from alkali metal cations, ammonium cations, and organic ammonium and sulfonium cations having in total 1–3 carbon atoms, and the mole ratio of such cationic counterions to the anionic exogenous chemical substance is preferably about 0.8:1 to about 1.2:1, for example approximately 1:1. A preferred anionic exogenous chemical substance useful in any of the above embodiments of the invention is N-phosphonomethylglycine.

A liquid, preferably aqueous, concentrate composition is also provided, which when diluted with a suitable amount of water forms a plant treatment composition as described above. A contemplated liquid concentrate composition contains in total at least about 5% by weight and up to about 40% or more by weight of the anionic exogenous chemical substance expressed as acid equivalent (a.e.).

Also provided is a process for making a liquid concentrate composition of the first embodiment of the invention, comprising a neutralizing step and a conditioning step.

The neutralizing step comprises neutralization of a first molar amount $X^1$ of an anionic exogenous chemical substance with a molar amount A of one or more amine compound(s) of formula (I) in a liquid, preferably aqueous, medium with agitation to make a neutralized composition containing one or more amphiphilic salt(s) of the exogenous chemical substance. For an exogenous chemical substance that forms only monobasic salts, the ratio $nA/X^1=1$, whereas for an exogenous chemical substance such as glyphosate that forms monobasic and dibasic salts, the ratio $nA/X^1$ can be in the range from 1 to 2. Optionally the neutralizing step further comprises introducing to the liquid medium, with agitation, a second molar amount $X^2$ of the exogenous chemical substance in the form of one or more salt(s) other than an amphiphilic salt formed by neutralizing the exogenous chemical substance with an amine compound of formula (I). Optionally and independently of the presence of the second molar amount, a third molar amount $X^3$ of the exogenous chemical substance is present in an acid form and is not neutralized. $X^1$ as a fraction of $(X^1+X^2+X^3)$ is about 0.05 to 1, preferably about 0.1 to 1. The salt(s) of the second molar amount of the exogenous chemical substance can be made in situ by neutralizing, in the liquid medium with agitation, this second molar amount with one or more base(s) other than an amine compound of formula (I), before, during or after neutralization of the first molar amount; alternatively such salt(s) can be prepared separately by processes known in the art and added to the liquid medium before, during or after neutralization of the first molar amount.

It is to be understood that the term "neutralizing" as used herein refers simply to the admixture of acid and base, and does not necessarily imply reaction of all of the acid and base to form a salt.

The conditioning step comprises continuing the agitation of the neutralized composition until supramolecular aggregates comprising amphiphilic salt(s) of the exogenous chemical substance formed by neutralizing the exogenous chemical substance with an amine compound of formula (I) are colloidally dispersed in the liquid medium.

An alternative process for making a liquid concentrate composition of the invention comprises a step of preparing a first concentrated aqueous solution or dispersion of a low molecular weight water-soluble salt of an anionic exogenous chemical substance, a step of preparing a second concentrated aqueous solution or dispersion of a salt of an amine compound of formula (I) with an acid other than an exogenous chemical substance, and a step of mixing the first and second concentrated solution or dispersion to form the liquid concentrate composition. Optionally the composition thus produced is adjusted by addition of water to obtain a desired final concentration of ingredients. The product of this alternative process can be tested by techniques disclosed herein for the presence of supramolecular aggregates colloidally dispersed in an aqueous medium, and by techniques known in the art for the presence of the exogenous chemical substance in such supramolecular aggregates and/or in the aqueous medium. The result of such tests will determine whether the product is a composition of the first or of the second embodiment as defined above. Regardless of the result of such tests, the product is a composition of the third embodiment as defined above.

A "concentrated" aqueous solution or dispersion as used in a process of the invention is defined herein as one having a concentration of at least about 5% by weight of the exogenous chemical substance, expressed as acid equivalent, or of the amine compound of formula (I), but not exceeding a maximum concentration above which the resulting composition would be unstable, nonhomogeneous or nonfluid (as, for example, a gel or paste). Typically a concentrated aqueous solution of a salt contains about 20% by weight to a maximum percentage by weight corresponding to the limit of solubility of the salt at 20° C.

The first concentrated aqueous solution or dispersion can be a product of commerce, such as for example MON 0139 of Monsanto Company, which is a 62% by weight aqueous solution of glyphosate isopropylammonium salt. Alternatively, the first concentrated aqueous solution or dispersion can be prepared by dissolving or dispersing a solid salt of the exogenous chemical substance in water, or by reacting the exogenous chemical substance in its acid form with a suitable low molecular weight base in an aqueous medium.

The second concentrated aqueous solution or dispersion can be a product of commerce, or it can be prepared by reacting an initially non-protonated amine compound of formula (I) in an aqueous medium with a suitable acid.

In the mixing step to prepare the concentrate liquid composition, the first aqueous solution or dispersion is added to the second aqueous solution or dispersion, or vice versa, preferably with agitation, in relative amounts calculated to provide a mole ratio of protonatable amino groups in the amine compound(s) of formula (I) to exogenous chemical substance of about 0.05:1 to about 2:1, preferably about 0.1:1 to about 1:1.

Variations of the above processes will be apparent to those of skill in the art. Compositions of the invention are not limited to those made by processes explicitly described herein.

Also provided is a process for eliciting a biological activity in a plant or in a pathogen, parasite or feeding organism present in or on the plant, comprising a step of applying to foliage of the plant a biologically effective amount of a plant treatment composition as provided herein.

Contemplated compositions have numerous benefits and advantages.

When applied to foliage of plants according to the process of the invention, a contemplated composition provides enhanced biological effectiveness by comparison with commercial standard formulations of the same exogenous chemical substance. At equal application rates of the exogenous chemical substance, a contemplated composition elicits a greater biological response than a commercial standard formulation. To obtain a given level of biological response, a lower application rate is required of the exogenous chemical substance when applied in the form of a contemplated composition than in the form of a commercial standard formulation.

A contemplated composition is biologically effective at a given application rate on a broader spectrum of target species than commercial standard formulations.

A contemplated composition provides greater reliability or consistency of biological effectiveness in a range of environmental conditions than commercial standard formulations.

A contemplated composition is more rainfast, i.e., its biological effectiveness is less likely to be reduced by incidence of rain or overhead irrigation occurring within a short period, for example up to about 6 hours, after application, than commercial standard formulations.

A contemplated composition provides an observable biological response in a shorter period after application than commercial standard formulations.

It will be understood that not all compositions of the invention possess all such benefits and advantages. However, at the least a composition of the invention provides a practical and effective alternative to previously known compositions.

DETAILED DESCRIPTION OF THE INVENTION

Exogenous Chemical Substances

Examples of anionic exogenous chemical substances that can be used in compositions of the present invention include, but are not limited to, chemical pesticides (such as herbicides, algicides, fungicides, bactericides, viricides, insecticides, aphicides, miticides, nematicides and molluscicides), plant growth regulators, fertilizers and nutrients, gametocides, defoliants, desiccants, mixtures thereof and the like. Although the disclosure herein relates to "an exogenous chemical substance", it is to be understood that more than one exogenous chemical substance can be included if desired in a composition of the invention.

A preferred group of anionic exogenous chemical substances consists of those that are normally applied post-emergence to foliage of plants, i.e., foliar-applied anionic exogenous chemical substances. An especially preferred group of foliar-applied anionic exogenous chemical substances consists of those that are systemic in plants, that is, translocated to some extent from their point of entry in the foliage to other parts of the plant where they can usefully exert their desired biological effect.

Especially preferred among these are herbicides, plant growth regulators and nematicides, particularly those that have a molecular weight, excluding counterions, of less than about 300.

Among such compounds, an even more preferred category consists of nematicides such as those disclosed in U.S. Pat. No. 5,389,680, the disclosure of which is incorporated herein by reference. Preferred nematicides of this group are 3,4,4-trifluoro-3-butenoic acid or N-(3,4,4-trifluoro-1-oxo-3-butenyl)glycine.

In one embodiment, the exogenous chemical substance is a herbicide. Suitable herbicides include, without restriction, acifluorfen, asulam, benazolin, bentazon, bilanafos, bromacil, bromoxynil, carfentrazone, chloramben, clopyralid, 2,4-D, 2,4-DB, dalapon, dicamba, dichlorprop, diclofop, endothall, fenac, fenoxaprop, flamprop, fluazifop, flumiclorac, fluoroglycofen, fomesafen, fosamine, glufosinate, glyphosate, haloxyfop, imazameth, imazamethabenz, imazamox, imazapic, imazapyr, imazaquin, imazethapyr, ioxynil, MCPA, MCPB, mecoprop, methylarsonic acid, naptalam, nonanoic acid, picloram, quinclorac, quizalofop, sulfamic acid, 2,3,6-TBA, TCA and triclopyr. Especially preferred herbicides are those whose molecular structure comprises at least one of each of amine, carboxylate, and either phosphonate or phosphinate functional groups. This category includes the herbicides N-phosphonomethylglycine (glyphosate) and DL-homoalanin-4-yl(methyl)phosphinate (glufosinate). Another preferred group of herbicides are those of the imidazolinone class, including imazameth, imazamethabenz, imazamox, imazapic, imazapyr, imazaquin and imazethapyr.

The invention is illustrated herein by particular reference to glyphosate. Although glyphosate has three acid sites, and can therefore form tribasic salts, preferred aqueous compositions have a pH value not greater than about 8, at which pH value the fraction of glyphosate existing as a tribasic salt is negligibly small. Only the two acid sites that are significantly deprotonated at pH 8 are therefore considered herein. One of these is on the phosphonate moiety, and the other is on the carboxylate moiety, of the glyphosate molecule.

For convenience and brevity herein, glyphosate acid is sometimes referred to as $GH_2$. Monovalent glyphosate anions, such as predominate for example at around pH 4, are referred to as $GH^-$. Divalent glyphosate anions, such as predominate for example at pH 7–8, are referred to as $G^{2-}$.

In plant treatment compositions of the invention, the amount of exogenous chemical substance present, in all forms thereof, is sufficient when applied to foliage of a plant to elicit the desired biological activity. Such compositions are sometimes referred to as "spray compositions", "sprayable compositions" or "ready-to-use compositions" and typically contain about 0.02% by weight to about 2% by weight of the exogenous chemical substance, expressed as acid equivalent (a.e.). For some purposes such compositions can contain up to about 5% a.e. by weight or even 10% a.e. by weight.

In liquid concentrate compositions of the invention, the amount of exogenous chemical substance present, in all forms thereof, provides, upon dilution in a suitable volume of water and application of the diluted composition to foliage of a plant, a sufficient amount to elicit the desired biological activity. Liquid concentrate compositions contain about 10% a.e. by weight to about 40% a.e. by weight or more of the exogenous chemical substance, in all forms thereof present.

As a significant portion of the cost of a packaged liquid concentrate composition is the volume-related cost of packaging, transport and storage, it is desirable to increase to the maximum practicable extent the concentration, or "loading", of exogenous chemical substance in the composition. Generally the factor that limits loading is physical stability of the composition under a range of storage conditions. The upper limit of loading depends on the nature and concentration of other ingredients in the composition and can be readily determined by routine experimentation using procedures known in the art.

In the first embodiment of the invention disclosed above, the exogenous chemical substance is present wholly or partly in the form of salt(s) having as the cationic counterion(s) one or more amine compound(s) of formula (I). In the second embodiment disclosed above, these salt(s) are not distinct identifiable component(s) of the composition, the exogenous chemical substance being introduced in the form of a low molecular weight salt or mixture of such salts. In preferred salts of this second embodiment the cationic counterion is monovalent and is selected from alkali metal cations, ammonium cations, and organic ammonium and sulfonium cations having in total 1–3 carbon atoms.

In particular where the exogenous chemical substance is glyphosate, illustrative cationic counterions suitable for use in compositions of the second embodiment of the invention are sodium, potassium, ammonium, dimethylammonium, isopropylammonium, monoethanolammonium and trimethylsulfonium cations.

Amine Compounds of Formula (I)

As indicated above, compositions of the invention contain one or more amine compound(s) each having the formula (I)

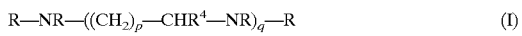

$$R-NR-((CH_2)_p-CHR^4-NR)_q-R \qquad (I)$$

wherein q is an integer of 0 to 9, each p is independently an integer of 1 to 5, each $R^4$ group is independently hydrogen or a $C_{1-5}$ hydrocarbyl group, and R groups are independently selected from hydrogen, $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide, ester, thioester and amide linkages, and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted.

In one preferred embodiment, an amine compound of formula (I) is selected having q=0, having one R group that is hydrogen or a $C_{1-5}$ alkyl group, and having two R groups that are independently $C_{6-22}$ hydrocarbyl chains, of which at least one is substituted and/or interrupted as described above. Thus the amine compound of this embodiment has the formula (II)

$$R^1-N\begin{matrix}R^2\\\\R^3\end{matrix} \qquad (II)$$

wherein R and $R^2$ are independently $C_{6-22}$ hydrocarbyl chains, at least one of which is (a) substituted at one or a plurality of carbon atoms with a functional group independently selected from hydroxyl, carboxy, carbamyl, mercapto and cyano groups and/or (b) interrupted by one or a plurality of functional linkages independently selected from ether, thioether, sulfoxide, ester, thioester and amide linkages and terminated by an uninterrupted hydrocarbyl segment having at least 6 carbon atoms, and $R^3$ is hydrogen or a $C_{1-5}$ hydrocarbyl group.

Preferably both hydrocarbyl chains $R^1$ and $R^2$ in an amine compound of formula (II) are so substituted and/or interrupted. Preferably each of $R^1$ and $R^2$ is substituted with 1 to about 5, more preferably only one, hydroxyl groups, or interrupted by 1 to about 5, more preferably only one, ether linkages. Preferably $R^1$ and $R^2$ each have about 12 to about 21 carbon atoms. Illustratively, $R^1$ and $R^2$ are each a 2-hydroxyalkyl or 2-hydroxyalkenyl group, or an alkyloxypropyl or alkenyloxypropyl group, wherein the terminal alkyl or alkenyl segments are linear chains having 12, 14, 16 or 18 carbon atoms, or are isodecyl or isotridecyl segments.

Alkyl or alkenyl segments are typically derived from lauric, myristic, palmitic, stearic, oleic, linolenic, linoleic or other natural fatty acids, with saturated chains such as lauryl, myristyl, palmityl or stearyl groups being preferred. $C_{12-15}$ branched or linear alkyl segments are another especially preferred type of terminal segment in an alkyloxypropyl group.

$R^3$ in an amine compound of formula (II) is preferably hydrogen or a methyl group.

In another preferred embodiment, an amine compound of formula (I) is selected having q=0, having two R groups that are independently hydrogen or $C_{1-5}$ alkyl groups, and having one R group that is a $C_{6-22}$ hydrocarbyl chain, substituted and/or interrupted as described above. Thus the amine compound of this embodiment has the formula (III)

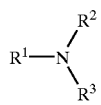
(III)

wherein $R^1$ is a $C_{6-22}$ hydrocarbyl chain which is (a) substituted at one or a plurality of carbon atoms with a functional group independently selected from hydroxyl, carboxy, carbamyl, mercapto and cyano groups and/or (b) interrupted by one or a plurality of functional linkages independently selected from ether, thioether, sulfoxide, ester, thioester and amide linkages and terminated by an uninterrupted hydrocarbyl segment having at least 6 carbon atoms, and $R^2$ and $R^3$ are independently hydrogen or $C_{1-5}$ hydrocarbyl groups.

Preferably $R^1$ is substituted with 1 to about 5, more preferably only one, hydroxyl groups, or interrupted by 1 to about 5, more preferably only one, ether linkages. Preferably $R^1$ has about 12 to about 21 carbon atoms. Illustratively, $R^1$ is a 2-hydroxyalkyl or 2-hydroxyalkenyl group, or an alkyloxypropyl or alkenyloxypropyl group, wherein the terminal alkyl or alkenyl segment is a linear chain having 12, 14, 16 or 18 carbon atoms, or is an isodecyl or isotridecyl segment. Alkyl or alkenyl segments are typically derived from lauric, myristic, palmitic, stearic, oleic, linolenic, linoleic or other natural fatty acids, with saturated chains such as lauryl, myristyl, palmityl or stearyl groups being preferred. $C_{12-15}$ branched or linear alkyl segments are another especially preferred type of terminal segment in an alkyloxypropyl group.

$R^2$ and $R^3$ in an amine compound of formula (III) are preferably identical and are preferably hydrogen or methyl groups.

In yet another preferred embodiment, an amine compound of formula (I) is selected having q=1–9. Thus the amine compound of this embodiment has the formula (IV)

$$R—NR—((CH_2)_p—CHR^4—NR)_q—R \qquad (IV)$$

wherein q is an integer of 1 to 9, each p is independently an integer of 1 to 5, each $R^4$ group is independently hydrogen or a $C_{1-5}$ hydrocarbyl group, and R groups are independently selected from hydrogen, $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide, ester, thioester and amide linkages and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted.

Preferably all R groups in an amine compound of formula (IV) that are $C_{6-22}$ hydrocarbyl or acyl chains are substituted with 1 to about 5, more preferably only one, hydroxyl groups, or interrupted by 1 to about 5, more preferably only one, ether linkages. Preferably each such R group has about 12 to about 21 carbon atoms. Illustratively, such an R group is a 2-hydroxyalkyl or 2-hydroxyalkenyl group, or an alkyloxypropyl or alkenyloxypropyl group, wherein the terminal alkyl or alkenyl segment is a linear chain having 12, 14, 16 or 18 carbon atoms, or is an isodecyl or isotridecyl segment. Alkyl or alkenyl segments are typically derived from lauric, myristic, palmitic, stearic, oleic, linolenic, linoleic or other natural fatty acids, with saturated chains such as lauryl, myristyl, palmityl or stearyl groups being preferred. $C_{12-15}$ branched or linear alkyl segments are another especially preferred type of terminal segment for an alkyloxypropyl group.

In preferred amine compounds of formula (IV), all $—((CH_2)_p—CHR^4—NR)—$ moieties are identical. Where p=1, $R^4$ is preferably hydrogen or a methyl group, but where p>1, $R^4$ is preferably hydrogen. Where p is 1 or 2, q is preferably 1 to 5, but where p>2, q is preferably 1 or 2.

Amine compounds of formula (IV) are derived by N-alkylation and/or N-acylation of compounds of formula (V)

$$NH_2—((CH_2)_p—CHR^4—NH)_q—H \qquad (V)$$

wherein p, q and $R^4$ are as defined for formula (IV). The terms "N-alkylation" and "N-acylation" embrace herein the addition of substituted and/or interrupted $C_{6-22}$ hydrocarbyl or acyl chains as described above. Particularly preferred amine compounds of formula (IV) are derived by N-alkylation and/or N-acylation of the following compounds of formula (V): ethylenediamine, 1,2-diaminopropane (otherwise known as propylenediamine), 1,3-diaminopropane (otherwise known as trimethylenediamine), 1,4-diaminobutane (otherwise known as butylenediamine), 1,6-diaminohexane (otherwise known as hexamethylenediamine), diethylenetriamine, triethylenetetramine, tetraethylenepentamine, bis(trimethylene)triamine (otherwise known as dipropylenetriamine), tris(trimethylene)tetramine (otherwise known as tripropylenetetramine), diethylenetriamine and bis(hexamethylene)triamine (otherwise known as dihexamethylenetriamine).

All amino groups in a compound of formula (V) are protonatable, and this is not altered by N-alkylation. However, N-acylation of an amino group results in formation of an amido group, which is non-protonatable. Thus, as an amine compound useful in compositions of the present invention must have at least one protonatable amino group, at least one of the amino groups must not be N-acylated.

N-acylation of a compound of formula (V) can, in a special case, result in formation of a compound having a succinimidyl function as shown in formula (VI):

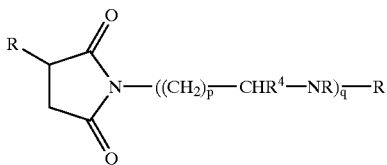

(VI)

where p, q, R and $R^4$ are as defined for formula (IV). The succinimidyl function can be derived from any one of the amino groups in the formula (V) compound; only one possibility, that where the succinimidyl function is derived from a terminal amino group, is shown in formula (VI). As the nitrogen atom of the succinimidyl group is non-protonatable, at least one of the other nitrogen atoms in the compound must remain protonatable. Such a compound, referred to herein as a succinimidyl compound, is embraced by the amine compounds useful in compositions of the present invention, and can be prepared by reacting an alkylsuccinic anhydride or alkenylsuccinic anhydride with a compound of formula (V) in a suitable solvent, typically with prolonged boiling.

N-alkylation of a compound of formula (V) can, in a special case, result in formation of a compound having an imidazolinyl function as shown in formula (VII):

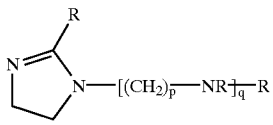

(VII)

where p, q, R and $R^4$ are as defined for formula (IV). Such a compound, referred to herein as an imidazolinyl compound, is embraced by the amine compounds useful in compositions of the present invention.

R groups in an amine compound of formula (IV) other than those that are $C_{6-22}$ hydrocarbyl or acyl chains, or substituted and/or interrupted $C_{6-22}$ hydrocarbyl or acyl chains as described above, are preferably hydrogen or methyl groups.

Normally, by design, only one amine compound of formula (I) is used in a composition of the invention. However, as the $C_{6-22}$ hydrocarbyl or acyl chain(s) or the terminal segment(s) of such chain(s) of the amine compound are often derived from natural sources such as coconut oil, palm oil, beef tallow, etc., commercial preparations of such amine compounds can contain a range of hydrocarbyl chain lengths, sometimes with varying degrees of unsaturation. Thus when amounts of an amine compound of formula (I) are specified herein, it is to be understood that such amounts are inclusive of other amine compounds of formula (I) present in the amine compound preparation used.

In compositions of the invention wherein an amine compound of formula (I) is introduced in the form of a salt thereof with an acid other than the exogenous chemical substance, at least one amino group of the amine compound is protonated and accompanied in aqueous solution or dispersion by one or more anionic counterions. Suitable counterions include without limitation chloride, bromide, iodide, sulfate, ethosulfate, phosphate, acetate, propionate, succinate, lactate, citrate and tartrate.

In such compositions, a salt of the amine compound wherein the anionic counterions are of the exogenous chemical substance itself can theoretically be present. Such a salt would be expected to behave in an aqueous medium as an amphiphilic species; for example, it would be expected, above a certain concentration, to self-assemble as supramolecular aggregates containing some fraction of the exogenous chemical substance present in the composition as a whole. However, it is not required by the present invention that such an amphiphilic salt be identifiably present as a distinct species, or that supramolecular aggregates are identifiably present, or that, if present, such supramolecular aggregates contain such amphiphilic salt.

Thus, in the second embodiment of the invention disclosed above, either substantially no supramolecular aggregates are present as determined by techniques disclosed herein, or supramolecular aggregates are present but contain no substantial amount of salt(s) of the amine compound(s) of formula (I) wherein the anionic counterion is the exogenous chemical substance, as determined by techniques known in the art.

For example, a composition of the invention can be made by adding a low molecular weight salt of an anionic exogenous chemical substance, such as isopropylammonium glyphosate, to an aqueous colloidal dispersion of supramolecular aggregates containing the hydrochloric acid salt of an amine compound of formula (I), such as N-(2-hydroxydodecyl)-N,N-dimethylammonium chloride. Using a chloride selective electrode, the concentration of free chloride ions in the aqueous medium can be determined before and after addition of the glyphosate salt. If the concentration of chloride ions does not increase, it can be concluded that substantially none of the chloride located in the supramolecular aggregates has been replaced by glyphosate and that therefore no substantial amount of glyphosate is located in the supramolecular aggregates. In this instance the composition conforms to the second embodiment of the invention. More likely an increase in chloride ion concentration in the aqueous medium will be recorded, from which it can be concluded that ion exchange has occurred in the supramolecular aggregates with the result that an amphiphilic salt of the amine compound of formula (I) with glyphosate is present in those aggregates. In this instance, the composition conforms to the first rather than the second embodiment of the invention.

It will be understood by those of skill in the art that the above procedure can be adapted for situations where the anionic counterion of the amine compound of formula (I) is other than chloride.

In the first embodiment, a composition of the invention contains amphiphilic salt(s) formed by neutralization of a first molar amount $X^1$ of the anionic exogenous chemical substance by one or more amine compound(s) of formula (I). Such compositions are disclosed herein as comprising a first and optionally a second and/or third molar amount of the exogenous chemical substance and are more fully described below.

Amphiphilic Salt(s) of the First Molar Amount of the Exogenous Chemical Substance Compositions of the first embodiment of the invention contain supramolecular aggregates comprising amphiphilic salt(s) formed by neutralization of a first molar amount $X^1$ of the anionic exogenous chemical substance by one or more amine compound(s) of formula (I).

For example, an amphiphilic monobasic salt of glyphosate with cations derived from an amine compound of formula (I) can be represented by formula (VIII):

  (VIII)

and a dibasic salt by formula (IX):

  (IX)

where n is the number of protonatable amino groups in the amine compound as described above and [$A^{n+}$] represents a fully protonated amine compound.

In some compositions of the first embodiment of the invention, the amphiphilic salt(s) of the exogenous chemical substance and one or more amine compound(s) of formula (I) are the only salts of the exogenous chemical substance present in the composition. In such compositions the first molar amount $X^1$ of the exogenous chemical substance represents all of the exogenous chemical substance present in salt form or accompanied by a base, i.e., $X^2=0$. The amount of [$A^{n+}$] present (including unprotonated amine compound coexisting with acid) in such compositions is about 1 mole per mole of exogenous chemical substance in the case of a monobasic salt, and about 2 moles per mole of exogenous chemical substance in the case of a dibasic salt. A mixture of monobasic and dibasic salts can be present, and in such a case the amount of [$A^{n+}$] present can range from about 1 to about 2 moles per mole of exogenous chemical substance. Where the exogenous chemical substance is glyphosate, a mixture of amphiphilic salts of formulas (VIII) and (IX) can be present, optionally together with glyphosate acid [$GH_2$] and/or with unprotonated amine compound.

For most purposes, even where the exogenous chemical substance is glyphosate, it is preferred that the monobasic salt predominate in a composition of the first embodiment; in other words, the amount of [$A^{n+}$] present (including unprotonated amine compound coexisting with acid) is not substantially greater than 1 mole per mole of exogenous chemical substance. At higher mole ratios of [$A^{n+}$] to exogenous chemical substance, it becomes more difficult to obtain the desired high loading of exogenous chemical substance in a concentrate composition. Thus in a glyphosate composition of the first embodiment where $X^2=0$, it is preferred that the amphiphilic salt of formula (VII) predominate. For example, it is preferred that the mole ratio of (VIII) to (IX) be about 80:20 to 100:0. This corresponds to a mole ratio of of [$A^{n+}$] to exogenous chemical substance of about 1:1 to about 1.2:1.

Where one or more salt(s) of a second molar amount of the exogenous chemical substance are present in a composition of the invention, i.e., $X^2>0$, the amount of amphiphilic salt(s) comprising [$A^{n+}$] cations is correspondingly reduced as a fraction of all salts of the exogenous chemical substance present. In general, to provide the benefits of the present invention, the amount of [$A^{n+}$] present should be sufficient to neutralize not less than about 10% of the exogenous chemical substance present, i.e., $X^1$ as a fraction of ($X^1+X^2+X^3$) is about 0.1 to 1.

In one embodiment of the invention, $X^1$ represents a relatively small fraction of ($X^1+X^2+X^3$), for example about 0.1 to about 0.3. In this embodiment, it is a primary objective to prepare a stable concentrate composition with a high loading of the exogenous chemical substance on an acid equivalent basis. As the amine compound(s) from which the [$A^{n+}$] cations are derived have relatively high molecular weight, it is difficult to achieve the desired high loading except where relatively low molecular weight cations, for example sodium, ammonium or isopropylammonium cations, forming salt(s) of the second molar amount $X^2$ of the exogenous chemical substance, predominate.

In another embodiment of the invention, $X^1$ represents a larger fraction of ($X^1+X^2+X^3$), for example about 0.3 to 1. In this embodiment, it is a primary objective to maximize the biological effectiveness of the composition, even if this means a relatively low loading of the exogenous chemical substance has to be accepted.

For clarity, it is re-emphasized that the molar amounts $X^1$, $X^2$ and $X^3$ as defined in the present specification and in the claims hereof are not determined by the amounts of the exogenous chemical substance which have donated protons to amine compound(s) of formula (I) or to other base(s). Instead, these molar amounts are determined simply by the molar amount of amine compound(s) of formula I and the molar amount, if any, of other base(s) present in the composition, provided there is no molar excess of base. This may be best explained by an illustrative example.

In this example, a plant treatment composition of the invention contains glyphosate at a concentration, in all acid and salt forms present, of 100 mM. Also present is N-(2-hydroxy)dodecyl-N,N-dimethylamine at a concentration (in total of protonated and unprotonated forms) of 25 mM, and sodium ions derived from sodium hydroxide at a concentration of 65 mM. Expressed as molar concentration, the first molar amount $X^1$ of the glyphosate is in this example equal by definition to the molar amount of N-(2-hydroxy)dodecyl-N,N-dimethylamine present, or 25 mM. The second molar amount $x^2$ of the glyphosate is equal by definition to the molar amount of sodium ions present, or 65 mM. The third molar amount $X^3$ of the glyphosate is determined by difference, i.e., (100 mM−25 mM−65 mM)=10 mM.

If a molar excess of base is present, the molar amount $X^3$ is defined herein to be zero.

Where the exogenous chemical substance is glyphosate, it is preferred that the total molar amount of base(s) added is not less than about half, and not greater than about two times, the total molar amount of glyphosate present. In other words, in a preferred composition:

if the total molar amount of glyphosate present, in all salt and acid forms, is g;

if the total molar amount of amine compound(s) of formula (I) present, in protonated and unprotonated forms, is a;

if the total molar amount of base(s) other than an amine compound of formula (I) present, in all forms, is b;

and if (a+b)/g is represented by Z; then 0.5<Z<2.

It is believed that in a typical concentrate liquid composition of the first embodiment of the invention, a significant fraction, for example more than about 10% by weight, preferably more than about 50% by weight, of an amphiphilic salt comprising [$A^{n+}$] cations is located in supramolecular aggregates which are colloidally dispersed in the liquid, preferably aqueous, medium. This can be verified by isolating the supramolecular aggregates from the medium by techniques known in the art such as filtration or centrifugation, and analyzing the two components thus obtained. Alternatively, by determining the CMC of the amphiphilic salt in water, the concentration, hence the total amount, of amphiphilic salt in the aqueous medium can be deduced, and the amount in the supramolecular aggregates determined by difference. Upon dilution of a concentrate composition in water to form a plant treatment composition, more of the amphiphilic salt(s) can be expected to be partitioned in the aqueous medium; however it is presently believed that even under these circumstances, in preferred compositions, most or substantially all of the amphiphilic salt(s) remain in the supramolecular aggregates.

Without being bound by theory, it is believed that location of a significant proportion of an exogenous chemical substance in supramolecular aggregates, as a result of the amphiphilic nature of salt(s) made by neutralizing the exogenous chemical substance with one or more amine compound(s) of formula (I), accounts at least in part for the superior biological effectiveness of compositions of the invention when applied to foliage of plants, through improved penetration into and through cuticles.

Salt(s) of the Second Molar Amount of the Exogenous Chemical Substance

The second molar amount $X^2$ in the present embodiment can be essentially zero. However, if a second molar amount of the exogenous chemical substance is present as one or more salt(s) other than a salt comprising $[A^{n+}]$ cations, such second molar amount can be present predominantly in supramolecular aggregates, predominantly in the aqueous medium, or in both. Such salt(s) can be amphiphilic or non-amphiphilic. Where a salt of the second molar amount is an amphiphilic salt, it is believed that it will be predominantly located in supramolecular aggregates. However, low molecular weight, non-amphiphilic, salts are preferred.

The cation(s) of salt(s) of the second molar amount of the exogenous chemical substance are provided by base(s) other than an amine compound of formula (I). Preferred such cations are monovalent cations including (i) alkali metal, for example sodium and potassium, cations, (ii) ammonium cations, (iii) organic ammonium and sulfonium cations having in total 1–6 carbon atoms, and (iv) trialkylammonium cations wherein alkyl groups each have 4–6 carbon atoms.

Particular examples of cations useful in salts of the second molar amount of the exogenous chemical substance include sodium, ammonium, dimethylammonium, isopropylammonium, monoethanolammonium, trimethylsulfonium and trihexylammonium cations. Low molecular weight salts, in which the cation has a molecular weight lower than about 100, are especially preferred.

Cation(s) of salt(s) of the second molar amount of an exogenous chemical substance are preferably monovalent and are sometimes referred to collectively herein as $[B^+]$. A monobasic salt of glyphosate, or a mixture of monobasic salts of glyphosate, with such cations can therefore be represented by formula (X):

$$[GH^-][B^+] \qquad (X)$$

and a dibasic salt or mixture thereof by formula (XI):

$$[G^{2-}][B^+]_2 \qquad (XI)$$

References herein to an amount of $[B^+]$ present should be understood to include any amount that may be present of un-ionized or undissociated base coexisting with the exogenous chemical substance in its acid form.

For most purposes, even where the exogenous chemical substance is glyphosate, it is preferred that the monobasic salt predominate in the composition, in other words, that the amount of $[B^+]$ present be not substantially greater than 1 mole per mole of exogenous chemical substance. At higher mole ratios of $[B^+]$ to exogenous chemical substance, it can become more difficult to obtain the desired high loading of exogenous chemical substance in a concentrate composition. Thus in a glyphosate composition of the invention where $X^2>0$, it is preferred that, in salt(s) of the second molar amount, salt(s) of formula (X) predominate. For example, it is preferred that the mole ratio of (X) to (XI) be about 80:20 to 100:0. This corresponds to a mole ratio of $[B^+]$ to the second molar amount $X^2$ of exogenous chemical substance of about 1:1 to about 1.2:1.

The Third Molar Amount of the Exogenous Chemical Substance

Optionally, a third molar amount $X^3$ of the exogenous chemical substance can be present in the form of the acid, unneutralized by any base. Typically, $X^3$ accounts for not more than about half of the total molar amount of the exogenous chemical substance present in all its forms. Preferably, $X^3$ is small by comparison with $(X^1+X^2)$, for example $X^3$ as a fraction of $(X^1+X^2+X^3)$ is not greater than about 0.1.

Characteristics of a Contemplated Composition

By selecting the particular amine compounds disclosed herein, the compositions exhibit a high degree of physical stability. Where colloidal dispersions of supramolecular aggregates are formed, these dispersions have surprisingly been found to exhibit a high degree of physical stability. The supramolecular aggregates themselves, as well as the composition as a whole, are physically stable, a feature which is of great benefit in the handling, storage and use of compositions of the invention.

A particularly unexpected discovery is that supramolecular aggregates present in preferred embodiments substantially maintain their structural integrity even upon dilution to levels useful for direct application to foliage of plants. This structural integrity is generally not dependent on the presence of dispersants or emulsifying agents, or indeed of any surfactants other than the amine compound(s) of formula (I) or amphiphilic salt(s) thereof. However, as indicated below, surfactants other than an amine compound of formula (I) or an amphiphilic salt thereof can optionally be present in a composition of the invention.

Certain aqueous concentrate compositions of the invention can be described as stable colloidal dispersions of supramolecular aggregates. By "stable" in this context it is meant that no phase separation occurs during storage of a composition without agitation at 20–25° C. for 48 hours. A stability test is described more fully in the Examples herein. The more desirable aqueous concentrate compositions of the invention are colloidal dispersions in which no phase separation occurs during storage without agitation at constant or varying temperatures from about 10° C. to about 40° C. for 48 hours, even more desirably from about 0° C. to about 50° C. for 7 days, and most desirably about –10° C. to about 60° C. for 30 days. Stability at elevated temperatures for short time periods provides a good indication of long-term stability under normal storage conditions; it is contemplated that certain concentrate compositions of the invention will be stable for periods of 1 year or more under normal storage conditions.

Supramolecular aggregates of compositions of the invention are sometimes referred to as nanoparticles. The term "nanoparticle" has no universally accepted definition in the art; however as used herein the term refers to bodies whose longest dimension is of a size up to about 1 μm (1000 nm), and includes bodies that are not solid particulates.

The supramolecular aggregates present in compositions of the invention are of at least two types. A first type is of a size too small to be detectable by transmission electron microscopy, but measurable by other techniques known in the art such as dynamic light scattering. Supramolecular aggregates of this first type have characteristics of more or less spherical micelles, colloidal dispersions of which in an aqueous medium are variously referred to as emulsions, microemulsions, micellar emulsions and micellar solutions. Unless the context demands otherwise, the term "emulsion" as descriptive of a composition of the present invention is herein reserved for compositions where the micelles or other supramolecular aggregates contain, in addition to amphiphilic salt(s) of an exogenous chemical substance, an oil as described in greater detail below. In the absence of such oil, the micelles, or supramolecular aggregates of the first type, typically have a mean diameter of about 1 to about 10 nm, most commonly about 2 to about 5 nm.

In common with other micellar dispersions, compositions of the invention exhibit a critical micelle concentration (CMC), which is a concentration of an amphiphilic material below which molecules of the amphiphilic material do not aggregate to form micelles. Compositions of the invention preferably have a CMC not greater than about 1000 $\mu$M, more preferably not greater than about 100 $\mu$m.

Compositions of the invention can also contain supramolecular aggregates of a second type. These are typically 20–100 nm in size and are normally spherical. They are too large to be simple micelles and are believed to be vesicular, multilamellar or liposome-like in structure.

Typically, concentrate compositions of the invention are clear or slightly turbid.

Other Optional Ingredients

Optionally, compositions of the invention can contain agriculturally acceptable materials other than an exogenous chemical substance or a salt thereof as described herein.

For example, more than one exogenous chemical substance can be included. An additional anionic exogenous chemical substance can be included, selected for example from those hereinbefore listed. Alternatively or in addition, an exogenous chemical substance that is other than anionic as defined herein can be included. For example, a glyphosate composition of the invention can optionally contain, in addition to glyphosate, an anionic herbicidal compound such as acifluorfen, asulam, benazolin, bentazon, bialaphos, carfentrazone, clopyralid, 2,4-D, 2,4-DB, dalapon, dicamba, dichlorprop, diclofop, fenoxaprop, flamprop, fluazifop, fluoroglycofen, fluroxypyr, fomesafen, fosamine, glufosinate, haloxyfop, imazameth, imazamethabenz, imazamox, imazapic, imazapyr, imazaquin, imazethapyr, MCPA, MCPB, mecoprop, methylarsonic acid, nonanoic acid, picloram, sulfamic acid, 2,3,6-TBA, TCA and triclopyr. Such additional anionic compound is present as salt(s) comprising [$A^{n+}$], and optionally [$B^+$], cations as described herein. Similarly, a composition of the invention containing salts of an anionic herbicide can optionally contain a herbicidal compound that is other than anionic, such as for example an ester derivative of an anionic herbicide, or a herbicide selected from acetochlor, aclonifen, alachlor, ametryn, amidosulfuron, anilofos, atrazine, azafenidin, azimsulfuron, benfluralin, benfuresate, bensulfuron-methyl, bensulide, benzofenap, bifenox, bromobutide, bromofenoxim, butachlor, butamifos, butralin, butroxydim, butylate, cafenstrole, carbetamide, carfentrazone-ethyl, chlomethoxyfen, chlorbromuron, chloridazon, chlorimuron-ethyl, chlorotoluron, chlornitrofen, chlorotoluron, chlorpropham, chlorsulfuron, chlorthal-dimethyl, chlorthiamid, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluchloralin, flumetsulam, flumiclorac-pentyl, flumioxazin, fluometuron, fluorochloridone, fluoroglycofen-ethyl, flupoxam, flurenol, fluridone, fluroxypyr-1-methylheptyl, flurtamone, fluthiacet-methyl, fomesafen, halosulfuron, haloxyfop-methyl, hexazinone, imazosulfuron, indanofan, isoproturon, isouron, isoxaben, isoxaflutole, isoxapyrifop, lactofen, lenacil, linuron, mefenacet, metamitron, metazachlor, methabenzthiazuron, methyldymron, metobenzuron, metobromuron, metolachlor, metosulam, metoxuron, metribuzin, metsulfuron, molinate, monolinuron, naproanilide, napropamide, naptalam, neburon, nicosulfuron, norflurazon, orbencarb, oryzalin, oxadiargyl, oxadiazon, oxasulfuron, oxyfluorfen, pebulate, pendimethalin, pentanochlor, pentoxazone, phenmedipham, piperophos, pretilachlor, primisulfuron, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, quinclorac, quinmerac, quizalofop-ethyl, rimsulfuron, sethoxydim, siduron, simazine, simetryn, sulcotrione, sulfentrazone, sulfometuron, sulfosulfuron, tebutam, tebuthiuron, terbacil, terbumeton, terbuthylazine, terbutryn, thenylchlor, thiazopyr, thifensulfuron, thiobencarb, tiocarbazil, tralkoxydim, triallate, triasulfuron, tribenuron, trietazine, trifluralin, triflusulfuron and vernolate.

Exogenous chemical substances useful in compositions of the invention can be selected from those listed in standard reference works such as *The Pesticide Manual,* 11th Edition, British Crop Protection Council (1997), and *Farm Chemicals Handbook '97,* Meister Publishing Company (1997).

Various agriculturally acceptable adjuvants or excipient substances can also be included, whether or not their purpose is to contribute directly to the biological effectiveness of an exogenous chemical substance in a treated plant. For example, where the exogenous chemical substance is a herbicide, liquid nitrogen fertilizer or ammonium sulfate can be included in the composition. In some instances it can be desirable to include microencapsulated acid in the composition, to lower the pH of a spray solution on contact with foliage.

Other optional components of compositions of the invention include agents to modify color, odor, viscosity, gelling properties, freezing point, stability or texture.

One or more surfactant(s), other than an amine compound of formula (I) or an amphiphilic salt thereof, can also be included in a contemplated composition. A wide range of surfactants is available to the formulator of exogenous chemical substances and can be selected readily from standard works such as *McCutcheon's Emulsifiers and Detergents,* 1997 Edition, MC Publishing Company, or *Handbook of Industrial Surfactants,* 2nd Edition, Gower (1997).

There is no restriction on the type or chemical class of surfactant that can be used. Nonionic, anionic, cationic and amphoteric types, or combinations of more than one of these types, are all useful in particular situations.

Many surfactants useful herein have a chemical structure that comprises one or more moieties each consisting of a single $C_{2-4}$ alkylene oxide unit or a polymerized or copolymerized chain of $C_{2-4}$ alkylene oxide units. Such surfactants are referred to as polyoxyalkylene surfactants and include nonionic, anionic, cationic and amphoteric types. Polyoxyalkylene surfactants useful in presently contemplated compositions contain about 2 to about 100 $C_{2-4}$ alkylene oxide units. In preferred polyoxyalkylene surfactants the alkylene oxide units form one or more chain(s) of either ethylene oxide or copolymerized ethylene oxide and propylene oxide, each chain of alkylene oxide units having a terminal hydrogen or a $C_{1-4}$ alkyl or $C_{2-4}$ acyl end-cap.

Hydrophobic moieties of surfactants useful in compositions of the invention can be essentially hydrocarbon-based, in which case the hydrophobic moieties are typically $C_{8-24}$, preferably $C_{12-18}$, alkyl, alkenyl, alkylaryl, alkanoyl or alkenoyl chains. These chains can be linear or branched. Alternatively, the hydrophobic moieties can contain silicon atoms, for example in the form of siloxane groups such as heptamethyltrisiloxane groups, or fluorine atoms, for example as partially fluorinated alkyl or perfluoroalkyl chains.

Among nonionic surfactants, especially preferred classes include polyoxyethylene alkyl, alkenyl or alkylaryl ethers, such as polyoxyethylene primary or secondary alcohols, alkylphenols or acetylenic diols; polyoxyethylene alkyl or alkenyl esters, such as ethoxylated fatty acids; sorbitan alkylesters, whether ethoxylated or not; glyceryl alkylesters; sucrose esters; and alkyl polyglycosides. Representative specific examples of such nonionic surfactants include polyoxyethylene (9) nonylphenol, Neodol™ 25-7 of Shell (a polyoxyethylene (7) $C_{12-15}$ linear primary alcohol), Tergitol™ 15-S-9 of Union Carbide (a polyoxyethylene (9) $C_{12-15}$ secondary alcohol), Tween™ 20 of ICI (a polyoxyethylene (20) sorbitan monolaurate), Surfynol™ 465 of Air Products (a polyoxyethylene (10) 2,4,7,9-tetramethyl-5-decyne-4,7-diol) and AgriMul™ PG-2069 of Henkel (a $C_{9-11}$ alkyl polyglucoside).

Among anionic surfactants, especially preferred classes include fatty acids, sulfates, sulfonates, and phosphate mono- and diesters of alcohols, alkylphenols, polyoxyethylene alcohols and polyoxyethylene alkylphenols, and carboxylates of polyoxyethylene alcohols and polyoxyethylene alkylphenols. These can be used in their acid form but are more typically used as salts, for example sodium, potassium or ammonium salts.

Among cationic surfactants, especially preferred classes include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) oxyethylene trimethylammonium chloride. Particularly preferred polyoxyethylene alkyletheramines are those disclosed in International Publication No. WO 96/32839.

Many cationic quaternary ammonium surfactants of diverse structures are known in the art to be useful in combination with glyphosate and other exogenous chemical substances and can be used in compositions contemplated herein; such quaternary ammonium surfactants have formula (XII):

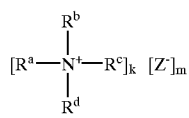

(XII)

where $Z^-$ is a suitable anion such as chloride, bromide, iodide, acetate, salicylate, sulfate or phosphate; k and m are integers such that the positive electrical charges on cations balance the negative electrical charges on anions; and options for $R^a$, $R^b$, $R^c$ and $R^d$ include, without limitation, the following:

(i) $R^a$ is a benzyl or $C_{8-24}$, preferably a $C_{12-19}$, alkyl or alkenyl group, and $R^b$, $R^c$ and $R^d$ are independently $C_{1-4}$ alkyl, preferably methyl, groups;

(ii) $R^a$ and $R^b$ are independently $C_{8-24}$, preferably $C_{12-18}$, alkyl or alkenyl groups, and $R^c$ and $R^d$ are independently $C_{1-4}$ alkyl, preferably methyl, groups;

(iii) $R^a$ is a $C_{8-24}$, preferably a $C_{12-18}$, alkyl or alkenyl group, $R^b$ is a polyoxyalkylene chain having about 2 to about 100 $C_{2-4}$ alkylene oxide units, preferably ethylene oxide units, and $R^c$ and $R^d$ are independently $C_{1-4}$ alkyl, preferably methyl, groups;

(iv) $R^a$ is a $C_{8-24}$, preferably a $C_{12-18}$, alkyl or alkenyl group, $R^b$ and $R^c$ are polyoxyalkylene chains having in total about 2 to about 100 $C_{2-4}$ alkylene oxide units, preferably ethylene oxide units, and $R^d$ is a $C_{1-4}$ alkyl, preferably a methyl, group; or (v) $R^a$ is a polyoxyalkylene chain having about 2 to about 100 $C_{2-4}$ alkylene oxide units in which $C_{3-4}$ alkylene oxide units, preferably propylene oxide units, predominate, and $R^b$, $R^c$ and $R^d$ are independently $C_{1-4}$ alkyl, preferably methyl or ethyl, groups. Particularly preferred quaternary ammonium surfactants of this type are those disclosed in U.S. Pat. No. 5,464,807.

In a preferred embodiment of the present invention, an amphiphilic quaternary ammonium compound, or mixture of such compounds, is present, having formula (XIII):

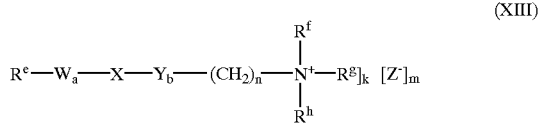

(XIII)

wherein $R^e$ is a hydrocarbyl or haloalkyl group having about 6 to about 22 carbon atoms; W and Y are independently O or NH; a and b are independently 0 or 1 but at least one of a and b is 1; X is CO, SO or $SO_2$; n is 2 to 4; $R^f$, $R^g$ and $R^h$ are independently $C_{1-4}$ alkyl; and k, m and $Z^-$ have the same meanings as in formula (XII). $R^e$ in one particular embodiment is a hydrocarbyl group having about 12 to about 18 carbon atoms. $R^e$ can also be fluorinated. In one specific embodiment, $R^e$ is perfluorinated, and preferably has about 6 to about 12 carbon atoms. In one particularly preferred embodiment, $R^e$ is a saturated perfluoroalkyl group having about 6 to about 12 carbon atoms, X is CO or $SO_2$, Y is NH, a is 0, b is 1, n is 3, $R^f$, $R^g$ and $R^h$ are methyl groups, k and m are each 1, and $Z^-$ is a chloride, bromide or iodide anion.

Sulfonylamino compounds of formula (XIII), i.e., those wherein X is $SO_2$, Y is NH, a is 0 and b is 1, are especially preferred. Suitable examples include 3-(((heptadecafluorooctyl)sulfonyl)amino)-N,N,N-trimethyl-1-propaminium iodide, available for example as Fluorad™ FC-135 from 3M Company, and the corresponding chloride. It is believed that Fluorad™ FC-754 of 3M Company comprises the corresponding chloride.

When included, amphiphilic quaternary ammonium compound(s) of formula (XIII) are preferably present in an adjuvant amount, i.e., an amount sufficient to provide visibly improved biological effectiveness of the exogenous chemical substance by comparison with a composition lacking such compound(s). "Visibly improved" in the present context means that, in a side-by-side comparison, a difference in biological effectiveness in favor of the composition containing the amphiphilic quaternary ammonium compound(s) would be evident to an experienced technician in the art relating to the particular class of exogenous chemical substance being applied, for example a weed scientist in the case where the exogenous chemical substance is a herbicide.

When present, one or more amphiphilic quaternary ammonium compound(s) of formula (XIII) are preferably included in a ratio of total weight of such compound(s) to weight of the anionic exogenous chemical substance, expressed as acid equivalent, of about 1:3 to about 1:100.

Suitable concentrations of a compound of formula (XIII) are about 0.001% to about 1% by weight in a plant treatment composition, and about 0.01% to about 10% by weight in a liquid concentrate composition of the invention.

Yet another class of excipient material that can be useful in compositions of the present invention is an oil, such as a triglyceride ester of fatty acids of animal, vegetable or synthetic origin, a paraffin, a polysiloxane, or a fatty acid or an ester or amide thereof. Such an oil, or mixture of oils, is present in an adjuvant amount as defined above. Examples of suitable oils include triglyceride esters of the coconut oil type, such as the product Miglyol™ 812 of Hüls, corn oil, olive oil, $C_{12-15}$ alkyl benzoate, eicosapentaenoic and docosahexaenoic acids and alkyl and triglyceride esters thereof and triglyceride ester of caprylic acid. Oils can be fractionated or not. Fractionation permits elimination of certain fatty acid chain lengths so as to modify melting point.

In a particular embodiment of the invention, one or more oil(s) are included, each having a chemical structure corresponding to formula (XIV):

$$R^{14}\text{—CO—Y—}R^{15} \quad\quad (XIV)$$

wherein $R^{14}$ is a hydrocarbyl group having about 5 to about 21 carbon atoms, $R^{15}$ is a hydrocarbyl group having 1 to about 14 carbon atoms, the total number of carbon atoms in $R^{14}$ and $R^{15}$ is about 11 to about 27, and Y is O or NH. $R^{14}$ and $R^{15}$ are preferably linear hydrocarbyl chains. $R^{14}$ preferably has about 11 to about 21 carbon atoms and is preferably derived from a natural saturated or unsaturated fatty acid. $R^{15}$ is preferably an alkyl group with 1 to about 6 carbon atoms. Especially preferred oils of formula (XIV) are therefore $C_{1-6}$ alkylesters or $C_{1-6}$ alkylamides of fatty acids. It is further preferred that $R^{14}$ is saturated in about 40% to 100% by weight of all compounds of formula (XIV) present in the composition.

In certain preferred embodiments, an oil is included that is a $C_{1-4}$ alkylester of a $C_{12-18}$ fatty acid, more preferably a $C_{1-4}$ alkylester of a $C_{12-18}$ saturated fatty acid. Examples include methyl oleate, ethyl oleate, isopropyl myristate, isopropyl palmitate and butyl stearate. Butyl stearate is especially preferred.

When present, one or more oil(s) of formula (XIV) are preferably included in a ratio of total weight of such oil(s) to weight of the cationic exogenous chemical substance, expressed as acid equivalent, of about 1:3 to about 1:100.

Suitable concentrations of an oil of formula (XIV) are about 0.001% to about 1% by weight in a plant treatment composition, and about 0.01% to about 10% by weight in a liquid concentrate composition of the invention.

Oil(s), if present, can be emulsified in a composition of the invention by means of the anionic compound(s) of formula (I) or amphiphilic salt(s) thereof. If desired, additional surfactant(s) can be included as emulsifier(s) for such oil(s). It is believed that the presence of oil, especially an oil of formula (XIV), in the composition can further enhance penetration of the exogenous chemical substance into or through plant cuticles, perhaps as a result of the more lipophilic character imparted to the composition.

The effect of including a suitable oil in a composition of the invention is generally to enlarge supramolecular aggregates to form swollen micelles or emulsion particles. In such a composition, the mean size of supramolecular aggregates can be within the range defined above for compositions lacking oil, or larger, for example up to about 1000 nm.

Process for Making a Composition of the Invention

Liquid concentrate compositions in accordance with the present invention can be prepared by the following general procedures; however, the invention is not limited to compositions made by these procedures.

In a suitable process, the first step is a neutralizing step. This step comprises neutralization of a first molar amount $X^1$ of an anionic exogenous chemical substance with one or more amine compound(s) of formula (I) in a liquid medium, preferably an aqueous medium, with agitation to make a liquid composition containing one or more amphiphilic salt(s) of the exogenous chemical substance. In an example of the neutralizing step where the exogenous chemical substance is glyphosate, a first molar amount $X^1$ of glyphosate acid ($GH_2$) is added to water together with an amine compound of formula (I), in an amount providing about 1 to about 2 moles of protonatable amino groups per mole of glyphosate, to make a monobasic salt $[GT^-]_n[A^{n+}]$, a dibasic salt $[G^{2-}]_n[A^{n+}]_2$ or a mixture of such monobasic and dibasic salts, where $[A^{n+}]$ is a cation derived by protonation of the amine compound. The relative molar proportions of monobasic and dibasic salts is a function of the quantity of the amine compound added per mole of glyphosate.

Optionally the neutralizing step further comprises introducing to the liquid composition, with agitation, a second molar amount $X^2$ of the exogenous chemical substance in the form of one or more salt(s) other than an amphiphilic salt formed by neutralizing the exogenous chemical substance with an amine compound of formula (I). In an example of this optional introduction as part of the neutralizing step where the exogenous chemical substance is glyphosate, a second molar amount $X^2$ of glyphosate is added in the form of a monobasic salt $[GH^-][B^+]$, a dibasic salt $[G^{2-}][B^{n+}]_2$, or a mixture of such monobasic and dibasic salts, where $[B^+]$ is a cation derived from a base other than an amine compound of formula (I).

Optionally a third molar amount $X^3$ of the exogenous chemical substance can be present during the neutralizing step, but is not neutralized, there being an insufficient amount of base(s) from which $[A^{n+}]$ and $[B^{n+}]$ cations are derived to neutralize all of the exogenous chemical substance present.

The salt(s) of the second molar amount of the exogenous chemical substance can be prepared separately in advance, or made in situ by neutralizing, in the liquid medium with agitation, this second molar amount with one or more base(s) other than an amine compound of formula (I). In either case, introduction of such salt(s) can occur before, during or after neutralization of the first molar amount of the exogenous chemical substance.

The neutralizing step takes place with agitation, preferably moderate agitation, for example using a magnetic stirrer. In a preferred embodiment, the neutralizing step is conducted at a temperature higher than the melting point of the amine compound(s) of formula (I) used. Typically the temperature of the liquid medium during the neutralizing step is about 50° C. to about 100° C.

In a suitable process, the second step is a conditioning step. This step comprises continuing the agitation of the liquid composition until supramolecular aggregates comprising amphiphilic salt(s) of the exogenous chemical substance formed by neutralizing the exogenous chemical substance with an amine compound of formula (I) are colloidally dispersed in the liquid medium. Agitation, preferably moderate agitation, can be provided, for example, by the same device used to agitate during the neutralizing step. It is preferred to maintain an elevated temperature, similar to that provided during the neutralizing step, throughout the conditioning step. The conditioning step can last for a period of a few minutes to a few hours and results in spontaneous formation of a stable colloidal dispersion of supramolecular aggregates, typically in the form of micelles and larger aggregates as described above.

Optional ingredients other than salt(s) of the exogenous chemical substance can be dissolved or dispersed in the liquid medium prior to, during or after the neutralization step and prior to, during or after the conditioning step. An optimum order of addition can readily be established for any composition by routine experimentation.

The product of the process just described is a composition of the first embodiment of the present invention.

An alternative process is illustrated with reference to glyphosate as the exogenous chemical substance. In a first step, a first concentrated aqueous solution is prepared comprising a low molecular weight salt of glyphosate. For example, the first concentrated aqueous solution can be prepared by neutralizing glyphosate acid in an aqueous medium with a suitable base such as sodium hydroxide, ammonia or isopropylamine. In a second step, a second concentrated aqueous solution or dispersion is prepared comprising an acid salt of an amine compound of formula (I). For example, the second concentrated aqueous solution or dispersion can be prepared by neutralizing the amine compound in an aqueous medium with a suitable acid such as hydrochloric acid, sulfuric acid or acetic acid. In a third step, the first concentrated aqueous solution and the second concentrated solution or dispersion are mixed to form a liquid concentrate composition of the invention.

The product of this alternative process is a composition of either the first or the second embodiment of the present invention, depending upon the results of testing of that composition as hereinbefore described.

Application of a Contemplated Composition to Foliage

Exogenous chemical substances should be applied to plants at a rate sufficient to give the desired effect. These application rates are usually expressed as amount of exogenous chemical substance per unit area treated, e.g. grams per hectare (g/ha). What constitutes a "desired effect" varies according to the standards and practice of those who investigate, develop, market and use a specific class of exogenous chemical substances. For example, in the case of a herbicide, the amount applied per unit area to give, consistently and reliably, at least 85% control of a plant species as measured by growth reduction or mortality is often used to define a commercially effective rate.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific exogenous chemical substance is within the skill of the ordinary agricultural scientist. Those of skill in the art will likewise recognize that individual plant conditions, weather and growing conditions, as well as the specific exogenous chemical substance and composition thereof selected, will influence the degree of biological effectiveness achieved in practicing this invention. Useful application rates for exogenous chemical substances employed can depend upon all of the above conditions. With respect to the use of the method of this invention for glyphosate herbicide, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

Herbicidal compositions of glyphosate or derivatives thereof are used to control a very wide variety of plants worldwide. Glyphosate compositions of the invention can be applied to a plant in a herbicidally effective amount, and can effectively control one or more plant species of one or more of the following genera without restriction: Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium and Zea.

Particularly important annual broadleaf species for which glyphosate compositions are used are exemplified without limitation by the following: velvetleaf (*Abutilon theophrasti*), pigweed (Amaranthus spp.), buttonweed (Borreria spp.), oilseed rape, canola, indian mustard, etc. (Brassica spp.), commelina (Commelina spp.), filaree (Erodium spp.), sunflower (Helianthus spp.), morningglory (Ipomoea spp.), kochia (*Kochia scoparia*), mallow (Malva spp.), wild buckwheat, smartweed, etc. (Polygonum spp.), purslane (Portulaca spp.), russian thistle (Salsola spp.), sida (Sida spp.), wild mustard (*Sinapis arvensis*) and cocklebur (Xanthium spp.).

Particularly important annual narrowleaf species for which glyphosate compositions are used are exemplified without limitation by the following: wild oat (*Avena fatua*), carpetgrass (Axonopus spp.), downy brome (*Bromus tectorum*), crabgrass (Digitaria spp.), barnyardgrass (*Echinochloa crus-galli*), goosegrass (*Eleusine indica*), annual ryegrass (*Lolium multiforum*), rice (*Oryza sativa*), ottochloa (*Ottochloa nodosa*), bahiagrass (*Paspalum notatum*), canarygrass (Phalaris spp.), foxtail (Setaria spp.), wheat (*Triticum aestivum*) and corn (*Zea mays*).

Particularly important perennial broadleaf species for which glyphosate compositions are used are exemplified without limitation by the following: mugwort (Artemisia spp.), milkweed (Asclepias spp.), canada thistle (*Cirsium arvense*), field bindweed (*Convolvulus arvensis*) and kudzu (Pueraria spp.).

Particularly important perennial narrowleaf species for which glyphosate compositions are used are exemplified without limitation by the following: brachiaria (Brachiaria spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (Phragmites spp.), johnsongrass (*Sorghum halepense*) and cattail (Typha spp.).

Other particularly important perennial species for which glyphosate compositions are used are exemplified without limitation by the following: horsetail (Equisetum spp.), bracken (*Pteridium aquilinum*), blackberry (Rubus spp.) and gorse (*Ulex europaeus*).

Thus, glyphosate compositions of the present invention, and a process for treating plants with such compositions, can be useful on any of the above species. In a particular contemplated process, a plant treatment composition of the invention comprising glyphosate in the form of one or more salt(s) thereof is applied to foliage of crop plants genetically transformed to tolerate glyphosate, and simultaneously to foliage of weeds or undesired plants growing in close proximity to such crop plants. This process results in control of the weeds or undesired plants while leaving the crop plants substantially unharmed. Crop plants genetically transformed to tolerate glyphosate include those whose seeds are sold by Monsanto or under license from Monsanto bearing the Roundup Ready® trademark. These include varieties of cotton, soybean, canola and corn.

Application of plant treatment compositions to foliage of plants is preferably accomplished by spraying, using any conventional means for spraying liquids, such as spray nozzles, atomizers, or the like. Compositions of the present invention can be used in precision farming techniques, in which apparatus is employed to vary the amount of exogenous chemical substance applied to different parts of a field, depending on variables such as the particular plant species present, soil composition, and the like. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon a number of factors, including the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

A contemplated process for eliciting a desired biological activity in a plant or in a pathogen, parasite or feeding organism present in or on a plant further comprises, prior to the step of applying a plant treatment composition of the invention to foliage of the plant, a step of diluting, in a suitable volume of water, a liquid concentrate composition as provided herein to form the plant treatment composition.

EXAMPLES

The following Examples are provided for illustrative purposes only and are not intended to limit the scope of the present invention. The Examples will permit better understanding of the invention and perception of its advantages and certain variations of execution.

Example 1

N,N-bis(2-hydroxyoctyl)-N-methylamine, abbreviated in tables herein as "2C8OH-NMe", is synthesized by the following procedure. In a 500 ml flask, 50 g 1,2-octene oxide is dissolved in 160 ml methanol. To the resulting solution is added 97.5 ml of a 2M solution of methylamine in methanol to form a reaction mixture. The reaction mixture is stirred for 1 hour at room temperature and then for a further 6 hours at 40° C. Upon evaporation of the methanol, 60 g N,N-bis(2-hydroxyoctyl)-N-methylamine as a yellow oil is obtained.

A composition of the invention is prepared by the following procedure. Into a 500 ml screw-capped vial are introduced 18.56 g N,N-bis(2-hydroxyoctyl)-N-methylamine synthesized as above and 12.18 g glyphosate acid, purity 98.5%. Deionized water in an amount of 209.26 g is added to provide an aqueous medium for neutralization of the glyphosate with the N,N-bis(2-hydroxyoctyl)-N-methylamine. The mixture is maintained for a processing time of 5 hours at 50° C. with stirring to ensure neutralizing and conditioning of the mixture to produce a homogeneous clear composition having a glyphosate a.e. concentration of 5.0% by weight. This is cooled to room temperature.

Upon dilution to a glyphosate a.e. concentration of 0.5% by weight, pH is found to be 4.5 and surface tension 29.5 mN m$^{-1}$. At this concentration, no supramolecular aggregates are observed. At the original concentration of 5.0% glyphosate a.e. by weight, supramolecular aggregates in the form of micelles are observed having a hydrodynamic diameter of 8 nm. The calculated mole ratio of protonatable amino groups to glyphosate is 0.91:1.

Example 2

N-(2-hydroxydodecyl)-N,N-dimethylamine, abbreviated in tables herein as "C12OH—NMe$_2$", is synthesized by the following procedure. In a 500 ml flask, 60 g 1,2-dodecene oxide is dissolved in 300 ml methanol. To the resulting solution is added, by injection over a 1-hour period, 14.7 g dimethylamine to form a reaction mixture. The reaction mixture is stirred for 4 hours at room temperature. Upon evaporation of the methanol, 70 g N-(2-hydroxydodecyl)-N,N-dimethylamine as a yellow oil is obtained.

A composition of the invention is prepared by the following procedure. Into a 500 ml screw-capped vial are introduced 21.0 g N-(2-hydroxydodecyl)-N,N-dimethylamine synthesized as above and 12.18 g glyphosate acid, purity 98.5%. Deionized water in an amount of 206.82 g is added to provide an aqueous medium for neutralization of the glyphosate with the N-(2-hydroxydodecyl)-N,N-dimethylamine. The mixture is maintained for a processing time of 5 hours at 50° C. with stirring to ensure neutralizing and conditioning of the mixture to produce a homogeneous clear composition having a glyphosate a.e. concentration of 5.0% by weight. This is cooled to room temperature.

Upon dilution to a glyphosate a.e. concentration of 0.5% by weight, pH is found to be 4.7 and surface tension 26.6 mN m$^{-1}$. Supramolecular aggregates in the form of micelles are observed having a hydrodynamic diameter of 7 nm. The calculated mole ratio of protonatable amino groups to glyphosate is 1.29:1.

Example 3

Dodecyloxypropylamine, abbreviated in Tables herein as "C12OC3-NH$_2$", is obtained as the commercial product PA-16 of Tomah. Into a 500 ml screw-capped vial are introduced 26.57 g dodecyloxypropylamine and 12.36 g glyphosate acid, purity 98.5%. Deionized water in an amount of 201.07 g is added to provide an aqueous medium for neutralization of the glyphosate with dodecyloxypropylamine. The mixture is maintained for a processing time of 5 hours at 50° C. with stirring to ensure neutralizing and conditioning of the mixture to produce a milky white homogeneous composition having a glyphosate a.e. concentration of 5.0% by weight. This is cooled to room temperature. The pH and size of supramolecular aggregates are measured upon dilution to 0.5% glyphosate a.e. by weight. Results are shown in Table 1 below.

Example 4

Isotridecyloxypropylamine, abbreviated in Tables herein as "C13bOC3-NH$_2$", is obtained as the commercial product PA-17 of Tomah. Into a 500 ml screw-capped vial are introduced 28.18 g isotridecyloxypropylamine and 12.36 g glyphosate acid, purity 98.5%. Deionized water in an amount of 199.46 g is added to provide an aqueous medium for neutralization of the glyphosate with isotridecyloxypropylamine. The mixture is maintained for a processing time of 5 hours at 50° C. with stirring to ensure neutralizing and conditioning of the mixture to produce a milky homogeneous composition having a glyphosate a.e. concentration of 5.0% by weight. This is cooled to room temperature. The pH and size of supramolecular aggregates are measured upon dilution to 0.5% glyphosate a.e. by weight. Results are shown in Table 1 below.

Example 5

Tetradecyloxypropylamine, abbreviated in Tables herein as "C14OC3-NH$_2$", is obtained as the commercial product PA-18 of Tomah. Into a 500 ml screw-capped vial are introduced 28.2 g tetradecyloxypropylamine and 12.36 g glyphosate acid, purity 98.5%. Deionized water in an amount of 198.72 g is added to provide an aqueous medium for neutralization of the glyphosate with isododecyloxypropylamine. The mixture is maintained for a processing time of 5 hours at 50° C. with stirring to ensure neutralizing and conditioning of the mixture to produce an opaque milky homogeneous composition having a glyphosate a.e. concentration of 5.0% by weight. This is cooled to room temperature. The pH and size of supramolecular aggregates are measured upon dilution to 0.5% glyphosate a.e. by weight. Results are shown in Table 1 below.

TABLE 1

Results for Examples 3–5

| Example | Amine compound | Mole ratio[1] | pH | Size of aggregates (nm) |
|---|---|---|---|---|
| 3 | C12OC3—NH$_2$ | 1.60:1 | 3.0 | 137 |
| 4 | C13bOC3—NH$_2$ | 1.45:1 | 3.0 | 403 |
| 5 | C14OC3—NH$_2$ | 1.41:1 | 3.2 | 60 |

[1]mole ratio of protonatable amino groups in amine compound of formula (I) to glyphosate a.e. (nA/X)

Example 6

N-(2-hydroxy)dodecyl bis(hexamethylene)triamine, abbreviated in Tables herein as "C12OH-DHTA", is synthesized by the following procedure. In a 500 ml flask, 20 g 1,2-dodecene oxide is added to 100 ml water. Then 47.2 g bis(hexamethylene)triamine, purity 99% (Aldrich) is added to form a reaction mixture. The reaction mixture is stirred for 3 hours at 75° C. The residue is recovered by adding 200 ml toluene and 50 ml ethanol, repeated three times. The organic phase is dried and evaporated and non-reacted bis(hexamethylene)triamine is withdrawn. On completion, 43.5 g N-(2-hydroxy)dodecyl bis(hexamethylene)triamine is obtained.

A composition of the invention is prepared by the following procedure. Into a 500 ml screw-capped vial are introduced 13.48 g N-(2-hydroxy)dodecyl bis(hexamethylene)triamine synthesized as above and 12.18-g glyphosate acid, purity 98.5%. Deionized water in an amount of 214.34 g is added to provide an aqueous medium for neutralization of the glyphosate with the N-(2-hydroxy) dodecyl bis(hexamethylene)triamine. The mixture is maintained for a processing time of 5 hours at 50° C. with stirring to ensure neutralizing and conditioning of the mixture to produce a homogeneous clear composition having a glyphosate a.e. concentration of 5.0% by weight. This is cooled to room temperature.

The pH, surface tension and size of supramolecular aggregates are measured upon dilution to 0.5% glyphosate a.e. by weight. Results are shown in Table 2 below.

Example 7

N-(2-hydroxy)hexadecyl triethylenetetramine, abbreviated in Tables herein as "C16OH-TETA", is synthesized by the following procedure. In a 500 ml flask, 50 g 1,2-hexadecene oxide is added to 400 ml methanol. Then 50.7 g triethylenetetramine hydrate, purity 98% (Aldrich) is added to form a reaction mixture. The reaction mixture is stirred for 6 hours under reflux. Upon evaporation of methanol, 43.5 g N-(2-hydroxy)hexadecyl triethylenetetramine is obtained.

A composition of the invention is prepared by the following procedure. Into a 500 ml screw-capped vial are introduced 10.48 g N-(2-hydroxy)hexadecyl triethylenetetramine synthesized as above and 12.18 g glyphosate acid, purity 98.5%. Deionized water in an amount of 217.34 g is added to provide an aqueous medium for neutralization of the glyphosate with N-(2-hydroxy)hexadecyl triethylenetetramine. The mixture is maintained for a processing time of 5 hours at 50° C. with stirring to ensure neutralizing and conditioning of the mixture to produce a homogeneous clear composition having a glyphosate a.e. concentration of 5.0% by weight. This is cooled to room temperature.

The pH, surface tension and size of supramolecular aggregates are measured upon dilution to 0.5% glyphosate a.e. by weight. Results are shown in Table 2 below.

Example 8

N-isotridecyloxypropyl trimethylenediamine, abbreviated in Tables herein as "C13bOC3-TDA", is obtained as the commercial product DA-17 of Tomah. Into a 500 ml screw-capped vial are introduced 14.09 g N-isotridecyloxypropyl trimethylenediamine and 12.36 g glyphosate acid, purity 98.5%. Deionized water in an amount of 213.55 g is added to provide an aqueous medium for neutralization of the glyphosate with the N-isotridecyloxypropyl trimethylenediamine. The mixture is maintained for a processing time of 5 hours at 50° C. with stirring to ensure neutralizing and conditioning of the mixture to produce a clear gold-colored homogeneous composition having a glyphosate a.e. concentration of 5.0% by weight. This is cooled to room temperature. The pH and size of supramolecular aggregates are measured upon dilution to 0.5% glyphosate a.e. by weight. Results are shown in Table 2 below.

Example 9

N-tetradecyloxypropyl trimethylenediamine, abbreviated in Tables herein as "C14OC3-TDA", is obtained as the commercial product DA-18 of Tomah. Into a 500 ml screw-capped vial are introduced 19.77 g N-tetradecyloxypropyl trimethylenediamine and 12.36 g glyphosate acid, purity 98.5%. Deionized water in an amount of 207.87 g is added to provide an aqueous medium for neutralization of the glyphosate with the N-isotridecyloxypropyl trimethylenediamine. The mixture is maintained for a processing time of 5 hours at 50° C. with stirring to ensure neutralizing and conditioning of the mixture to produce a clear colorless homogeneous composition having a glyphosate a.e. concentration of 5.0% by weight. This is cooled to room temperature. The pH and size of supramolecular aggregates are measured upon dilution to 0.5% glyphosate a.e. by weight. Results are shown in Table 2 below.

TABLE 2

Results for Examples 6–9

| Example | Amine compound | Mole ratio[1] | pH | Size of aggregates (nm) | Surface tension (mN/m) |
|---|---|---|---|---|---|
| 6 | C12OH—DHTA | 1:1 | 5.1 | 7 | 27.5 |
| 7 | C16OH—TETA | 1:1 | 5.3 | 45 | 39.7 |
| 8 | C13bOC3—TDA | 1:1 | 4.6 | 8/130 | not determined |
| 9 | C14OC3—TDA | 2:1 | 4.0 | 90 | not determined |

[1] mole ratio of protonatable amino groups in amine compound of formula (I) to glyphosate a.e. (nA/X)

Example 10

N-dodecylthioethyl-N,N-dimethylamine, abbreviated in Tables herein as "C12SC2-NMe$_2$", is used to prepare a glyphosate composition of the invention by a procedure similar to that for Examples 3–5.

Example 11

The compositions of Examples 1–10 are evaluated for herbicidal effectiveness in a greenhouse test by foliar application to a representative annual broadleaf species, velvetleaf (*Abutilon theophrasti*, ABUTH) and a representative annual narrowleaf species, Japanese millet, a form of barnyardgrass (*Echinochloa crus-galli*, ECHCF). For comparative purposes, the following commercial standard formulations are included in the test:

MON 0139, an aqueous solution of the mono (isopropylammonium) salt of glyphosate, containing 62% by weight of said salt and no other formulation ingredients except water, available from Monsanto Company; and Roundup® Ultra herbicide, an aqueous solution concentrate formulation of the mono(isopropylammonium) salt of glyphosate, containing 41% by weight of said salt together with a surfactant, this product being sold as an agricultural herbicide by Monsanto Company in the U.S.A.

MON 0139 contains glyphosate at a concentration of about 680 grams of acid equivalent per liter (g a.e./l) and Roundup® Ultra herbicide contains 356 g a.e./l.

The following procedure is used for the greenhouse test.

Seeds of the plant species indicated are planted in 85 mm square pots in a soil mix which has previously been steam sterilized and prefertilized with a 14-14-14 NPK slow release fertilizer at a rate of 3.6 kg/m$^3$. The pots are placed in a greenhouse with sub-irrigation. About one week after emergence, seedlings are thinned as needed, including removal of any unhealthy or abnormal plants, to create a uniform series of test pots.

The plants are maintained for the duration of the test in the greenhouse where they receive a minimum of 14 hours of light per day. If natural light is insufficient to achieve the daily requirement, artificial light with an intensity of approximately 475 microeinsteins is used to make up the difference. Exposure temperatures are not precisely controlled but average about 27° C. during the day and about 18° C. during the night. Plants are sub-irrigated throughout the test to ensure adequate soil moisture levels. Relative humidity is maintained at about 50% for the duration of the test.

Pots are assigned to different treatments in a fully randomized experimental design with 3 replications. A set of pots is left untreated as a reference against which effects of the treatments can later be evaluated. Two sets of 3 replications are provided for treatments with Roundup® Ultra, to ensure a sound basis is available for comparison of herbicidal effectiveness of compositions of the invention.

Application of glyphosate compositions to foliage is made by spraying with a track sprayer fitted with a TeeJet™ 9501E nozzle calibrated to deliver a spray volume of 93 liters per hectare (l/ha) at a pressure of 166 kilopascals (kPa). Application is made when the plants are 2–3 weeks old. After treatment, pots are returned to the greenhouse until ready for evaluation, in this Example 11 days after treatment (DAT).

Treatments are made using dilute aqueous compositions, prepared by dilution with water of preformulated concentrate compositions. All comparisons are made at equal glyphosate acid equivalent rates. The required degree of dilution for a glyphosate concentrate composition to make a plant treatment composition is calculated from the equation $$A = RS/VC$$

where A is the volume in milliliters (ml) of the glyphosate composition to be added to the plant treatment composition being prepared, R is the desired glyphosate rate in grams of acid equivalent per hectare (g a.e./ha), S is the total volume in milliliters (ml) of plant treatment composition being prepared, V is the application rate in liters per hectare (l/ha) of plant treatment composition, conventionally referred to as "spray volume", and C is the concentration of glyphosate in grams of acid equivalent per liter (g a.e./l) in the glyphosate composition.

For evaluation of herbicidal effectiveness, all plants in the test are examined by a single practiced technician, who records percent inhibition, a visual measurement of the effectiveness of each treatment by comparison with untreated plants. Inhibition of 0% indicates no effect, and inhibition of 100% indicates that all of the plants are completely dead. Inhibition of 85% or more is in most cases considered acceptable for normal herbicidal use; however in greenhouse tests such as the one described in this Example it is normal to apply compositions at rates which are expected to give less than 85% inhibition, as this makes it easier to discriminate among compositions having different levels of effectiveness.

Results of the test of Example 11 are given in Table 3 below.

TABLE 3

Herbicidal effectiveness data for Example 11

| Glyphosate composition | Glyphosate rate g a.e./ha | % Inhibition ABUTH | % Inhibition ECHCF |
|---|---|---|---|
| MON 0139 | 50 | 0 | 0 |
| | 100 | 5 | 15 |
| | 200 | 70 | 58 |
| | 400 | 80 | 65 |
| | 600 | 87 | 71 |

TABLE 3-continued

Herbicidal effectiveness data for Example 11

| Glyphosate composition | Glyphosate rate g a.e./ha | % Inhibition ABUTH | ECHCF |
|---|---|---|---|
| Roundup ® Ultra (first set) | 50 | 0 | 7 |
|  | 100 | 70 | 60 |
|  | 200 | 85 | 83 |
|  | 400 | 93 | 92 |
|  | 600 | 99 | 97 |
| Roundup ® Ultra (second set) | 50 | 0 | 3 |
|  | 100 | 70 | 59 |
|  | 200 | 83 | 76 |
|  | 400 | 96 | 91 |
|  | 600 | 97 | 97 |
| Example 1: 2C8OH—NMe | 50 | 0 | 5 |
|  | 100 | 47 | 42 |
|  | 200 | 77 | 50 |
|  | 400 | 87 | 77 |
|  | 600 | 97 | 85 |
| Example 2: C12OH—NMe$_2$ | 50 | 0 | 20 |
|  | 100 | 0 | 40 |
|  | 200 | 75 | 55 |
|  | 400 | 92 | 75 |
|  | 600 | 95 | 86 |
| Example 3: C12OC3—NH$_2$ | 50 | 0 | 3 |
|  | 100 | 5 | 43 |
|  | 200 | 77 | 50 |
|  | 400 | 88 | 68 |
|  | 600 | 94 | 77 |
| Example 4: C13bOC3—NH$_2$ | 50 | 0 | 5 |
|  | 100 | 12 | 47 |
|  | 200 | 75 | 53 |
|  | 400 | 88 | 68 |
|  | 600 | 93 | 78 |
| Example 5: C14OC3—NH$_2$ | 50 | 0 | 38 |
|  | 100 | 13 | 50 |
|  | 200 | 77 | 63 |
|  | 400 | 92 | 75 |
|  | 600 | 95 | 78 |
| Example 6: C12OH—DHTA | 50 | 0 | 0 |
|  | 100 | 0 | 38 |
|  | 200 | 63 | 50 |
|  | 400 | 77 | 78 |
|  | 600 | 82 | 87 |
| Example 7: C16OH—TETA | 50 | 0 | 2 |
|  | 100 | 0 | 3 |
|  | 200 | 5 | 33 |
|  | 400 | 60 | 50 |
|  | 600 | 75 | 55 |
| Example 8: C13bOC3—TDA | 50 | 0 | 0 |
|  | 100 | 23 | 43 |
|  | 200 | 57 | 53 |
|  | 400 | 83 | 73 |
|  | 600 | 85 | 85 |
| Example 9: C14O3—TDA | 50 | 0 | 2 |
|  | 100 | 3 | 30 |
|  | 200 | 63 | 43 |
|  | 400 | 80 | 50 |
|  | 600 | 83 | 52 |
| Example 10: C12SC2—NMe$_2$ | 50 | 0 | 45 |
|  | 100 | 57 | 55 |
|  | 200 | 85 | 70 |
|  | 400 | 94 | 70 |
|  | 600 | 97 | 77 |

The preceding description of specific embodiments of the present invention is not intended to be a complete list of every possible embodiment of the invention. Persons skilled in this field will recognize that modifications can be made to the specific embodiments described here that remain within the scope of the present invention.

What is claimed is:

1. A plant treatment composition for application to foliage of a plant to elicit a biological response, comprising an agronomically acceptable liquid carrier, wherein are dissolved or dispersed an anionic exogenous chemical substance and one or more amine compound(s) each having a number n of protonatable amino groups, n being at least 1, and having the formula (I)

$$R-NR-((CH_2)_p-CHR^4-NR)_q-R \quad (I)$$

wherein q is an integer of 0 to 9, each p is independently an integer of 1 to 5, each $R^4$ group is independently hydrogen or a $C_{1-5}$ alkyl group, and R groups are independently selected from hydrogen, $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide and thioester linkages, and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted; said exogenous chemical substance being present in the composition in an amount sufficient to elicit the biological response when the composition is applied to the foliage of the plant at a rate from about 10 to about 1000 liters per hectare (l/ha); and said amine compound(s) being present in the composition in an amount such that the mole ratio of protonatable amino groups in such compound(s) to the exogenous chemical substance is about 0.05:1 to about 2:1.

2. The composition of claim 1 wherein the carrier is water.

3. A liquid concentrate composition suitable for dilution in water to form the plant treatment composition of claim 2, comprising about 5% to about 40% by weight of the exogenous chemical substance expressed as acid equivalent.

4. The composition of claim 1 wherein the mole ratio of protonatable amino groups in said amine compound(s) to the exogenous chemical substance is about 0.1:1 to about 1:1.

5. The composition of claim 1 that comprises an aqueous application medium, wherein are colloidally dispersed supramolecular aggregates, comprising one or more amphiphilic salt(s) having anions of the anionic exogenous chemical substance and cations derived by protonation of said amine compound(s); said amphiphilic salt(s), including any fraction thereof existing outside said supramolecular aggregates, comprising about 5 to 100 mole percent of the exogenous chemical substance present in the composition; the balance to 100 mole percent of the exogenous chemical substance being present in the form of one or more salt(s) having cations contributed by base(s) other than an amine compound of formula (I), and/or in acid form.

6. The composition of claim 5 wherein said amphiphilic salt(s) comprise about 10 to 100 mole percent of the exogenous chemical substance present in the composition.

7. The composition of claim 5 wherein less than about 10 mole percent of the exogenous chemical substance in the composition is present in acid form.

8. The composition of claim 5 wherein cations contributed by base(s) other than an amine compound of formula (I) are selected from alkali metal cations, ammonium cations, organic ammonium or sulfonium cations having in total 1–6 carbon atoms, and trialkylammonium cations wherein alkyl groups each have 4–6 carbon atoms.

9. The composition of claim 1 that comprises an aqueous application medium, wherein are dissolved or dispersed the anionic exogenous chemical substance and said amine compound(s); said composition having substantially no amphiphilic salt of the exogenous chemical substance in supramolecular aggregates.

10. The composition of claim 9 wherein the exogenous chemical substance is present as a water-soluble salt having cationic counterions of molecular weight lower than about 100, and wherein each of said amine compound(s) is present as a salt formed with an acid that is not an exogenous chemical substance.

11. The composition of claim 10 wherein the cationic counterions of said water-soluble salt are selected from alkali metal cations, ammonium cations, and organic ammonium and sulfonium cations having in total 1–3 carbon atoms.

12. The composition of claim 1 wherein q is 1 to 9.

13. The composition of claim 12 wherein each R group that is a $C_{6-22}$ hydrocarbyl or acyl chain is substituted with one hydroxyl group or interrupted by one ether linkage.

14. A plant treatment composition for application to foliage of a plant to elicit a biological response, comprising an agronomically acceptable liquid carrier, wherein are dissolved or dispersed an anionic exogenous chemical substance and one or more amine compound(s) having the formula $$N(R)_3$$

wherein one R group is hydrogen or a $C_{1-5}$ alkyl group, and two R groups are independently $C_{6-22}$ hydrocarbyl chains, of which at least one is substituted at one or a plurality of carbon atoms with a functional group independently selected from hydroxyl, carboxy, carbamyl, mercapto and cyano groups and/or interrupted by one or a plurality of functional linkages independently selected from ether, thioether, sulfoxide and thioester linkages and terminated by an uninterrupted hydrocarbyl segment having at least 6 carbon atoms; said exogenous chemical substance being present in the composition in an amount sufficient to elicit the biological response when the composition is applied to the foliage of the plant at a rate from about 10 to about 1000 liters per hectare (l/ha); and said amine compound(s) being present in the composition in an amount such that the mole ratio of protonatable amino groups in such compound(s) to the exogenous chemical substance is about 0.05:1 to about 2:1.

15. The composition of claim 14 wherein each of said two R groups that are $C_{6-22}$ hydrocarbyl chains is substituted with one hydroxyl group or interrupted by one ether linkage.

16. A plant treatment composition for application to foliage of a plant to elicit a biological response, comprising an agronomically acceptable liquid carrier, wherein are dissolved or dispersed an anionic exogenous chemical substance and one or more amine compound(s) each having a number n of protonatable amino groups, n being at least 1, and having the formula (I)

$$R\text{—}NR\text{—}((CH_2)_p\text{—}CHR^4\text{—}NR)_q\text{—}R \qquad (I)$$

wherein q is 0, each p is independently an integer of 1 to 5, each $R^4$ group is independently hydrogen or a $C_{1-5}$ alkyl group, and R groups are independently selected from hydrogen, $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide, ester and thioester linkages, and terminated by an uninterrupted hydrocarbyl segment having at least 6 carbon atoms; with the proviso that two R groups are independently hydrogen or $C_{1-5}$ alkyl groups, and one R group is a $C_{6-22}$ hydrocarbyl chain, substituted at one or a plurality of carbon atoms with a functional group independently selected from hydroxyl, carboxy, carbamyl, mercapto and cyano groups and/or interrupted by one or a plurality of functional linkages independently selected from ether, thioether, sulfoxide, ester, thioester and amide linkages and terminated by an uninterrupted hydrocarbyl segment having at least 6 carbon atoms; said exogenous chemical substance being present in the composition in an amount sufficient to elicit the biological response when the composition is applied to the foliage of the plant at a rate from about 10 to about 1000 liters per hectare (l/ha); and said amine compound(s) being present in the composition in an amount such that the mole ratio of protonatable amino groups in such compound(s) to the exogenous chemical substance is about 0.05:1 to about 2:1.

17. The composition of claim 16 wherein said $C_{6-22}$ hydrocarbyl chain is substituted with one hydroxyl group or interrupted by one ether linkage.

18. A plant treatment composition for application to foliage of a plant to elicit a biological response, comprising an agronomically acceptable liquid carrier, wherein are dissolved or dispersed an anionic exogenous chemical substance and one or more amine compound(s) each having a number n of protonatable amino groups, n being at least 1, and having the formula (I)

$$R\text{-}NR\text{-}((CH_2)p\text{-}CHR^4\text{-}NR)_q\text{-}R \qquad (I)$$

wherein q is an interger of 0 to 9, each p is independently an integer of 1 to 5, each $R^4$ group is independently hydrogen or a $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide and thioester linkages, and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted, said exogenous chemical substance being N-phosphonomethylglycine or a salt thereof and being present in the composition in an amount sufficient to elicit the biological response when the composition is applied to the foliage of the plant at a rate from about 10 to about 1000 liters per hectare (l/ha); and said amine compound(s) being present in the composition in an amount such that the mole ratio of protonatable amino groups in such compound(s) to the exogenous chemical substance is abount 0.05:1 to about 2:1.

19. The composition of claim 18 that comprises an aqueous application medium, wherein are colloidally dispersed supramolecular aggregates, comprising one or more amphiphilic salt(s) having anions of the anionic exogenous chemical substance and cations derived by protonation of said amine compound(s); said amphiphilic salt(s), including any fraction thereof exisiting outside said supermolecular aggregates, comprising about 5 to 100 mole percent of the exogenous chemical substance present in the composition; the balance to 100 mole percent of the exogenous chemical substance being present in the form of one or more salt(s) having cations contributed by base(s) other than an amine compound of formula (I), and/or in acid form.

20. The composition of claim 18 wherein each R group that is a $C_{6-22}$ hydrocarbyl or acyl chain is substituted with one hydroxyl group or interrupted by one ether linkage.

21. A liquid concentrate composition suitable for dilution in water to form the plant treatment composition of claim 18, comprising about 5% to about 40% by weight of the exogenous chemical substance expressed as acid equivalent.

22. A plant treatment composition for application to foliage of a plant to elicit a biological response, comprising an agronomically acceptable liquid carrier, wherein are dissolved or dispersed an anionic exogenous chemical substance and one or more amine compound(s) having the formula

wherein one R group is hydrogen or a $C_{1-5}$ alkyl group, and two R groups are independently $C_{6-22}$ hydrocarbyl chains, of which at least one substituted at one or am plurality of carbon atoms with a functional group independently selected from hydroxyl, carboxy, carbamyl, mercapto and cyano groups and/or interrupted by one or a plurality of functional linkages independently selected from ether, thioether, sulfoxide and thioester linkages and terminated by an uninterrupted hydrocrabyl segment having at least 6 carbon atoms; said exogenous chemical substance being N- phosphonomethylglycine or a salt thereof and beig present in the composition in an amount sufficient to elicit the biological response when the composition is applied to the foliage of the plant at a rate from about 10 to about 1000 liters per hectare (I/ha); and said amine compound(s) being present in the composition in an amount such that the mole ratio of protonatable amino groups in such compound(s) to the exogenous chemical substance is about 0.05:1 to about 2:1.

23. The composition of claim 22 wherein each of said two R groups that are $C_{6-22}$ hydrocarbyl chains is substituted with one hydroxyl group or interrupted by one ether linkage.

24. A liquid concentrate composition suitable for dilution in water to form the plant treatment composition of claim 22, comprising about 5% to about 40% by weight of the exogenous chemical substance expressed as acid equivalent.

25. A plant treatment composition for application to foliage of a plant to elicit a biological response, comprising an agronomically acceptable liquid carrier, wherein are dissolved or dispersed an anionic exogenous chemical substance and one or more amine compound(s) having the formula

wherein two R groups are independently hydrogen or a $C_{1-5}$ alkyl groups, and one R groups is is a $C_{6-22}$ hydrocarbyl chain, substituted at one or a plurality of carbon atoms with a functional group independently selected from hydroxyl, carboxy, carbamyl, mercapto and cyano groups and/or interrupted by one or a plurality of functional linkages and terminated by an uninterrupted hydrocrabyl segment having at least 6 carbon atoms; said exogenous chemical substance being N- phosphonomethylglycine or a salt thereof and beig present in the composition in an amount sufficient to elicit the biological response when the composition is applied to the foliage of the plant at a rate from about 10 to about 1000 liters per hectare (I/ha); and said amine compound(s) being present in the composition in an amount such that the mole ratio of protonatable amino groups in such compound(s) to the exogenous chemical substance is about 0.05:1 to about 2:1.

26. The composition of claim 25 wherein said $C_{6-22}$ hydrocarbyl chain is substituted with one hydroxyl group or interrupted by one ether linkage.

27. A liquid concentrate composition suitable for dilution in water to form the plant treatment composition of claim 25, comprising about 5% to about 40% by weight of the exogenous chemical substance expressed as acid equivalent.

28. A process for eliciting a biological activity in a plant or in a pathogen, parasite or feeding organism present in or on the plant, comprising a step of applying to foliage of the plant a biologically effective amount of a plant treatment composition of claim 1.

29. A process for eliciting a biological activity in a plant or in a pathogen, parasite or feeding organism present in or on the plant, comprising a step of applying to foliage of the plant a biologically effective amount of a plant treatment composition of claim 14.

30. A process for eliciting a biological activity in a plant or in a pathogen, parasite or feeding organism present in or on the plant, comprising a step of applying to foliage of the plant a biologically effective amount of a plant treatment composition of claim 16.

31. A process for killing or controlling undesired plants comprising a step of applying to foliage of the plants a herbicidally effective amount of a plant treatment composition of claim 18.

32. A process for killing or controlling undesired plants comprising a step of applying to foliage of the plants a herbicidally effective amount of a plant treatment composition of claim 22.

33. A process for killing or controlling undesired plants comprising a step of applying to foliage of the plants a herbicidally effective amount of a plant treatment composition of claim 25.

34. A process for making a liquid concentrate composition suitable for dilution in water to form a plant treatment composition, comprising (1) a neutralizing step, wherein, with agitation in water, a first molar amount $X^1$ of an anionic exogenous chemical substance is neutralized with a molar amount A of one or more amine compound(s) each having a number $n$ of protonatable amino groups, $n$ being at least 1, and having the formula (I)

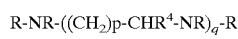

wherein q is an integer of 0 to 9, each p is independently an interger of 1 to 5, each $R^4$ group is independently hydrogen or a $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide and thioester linkages, and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted, said exogenous chemical substance being N-phosphonomethylglycine or a salt thereof and being present in the composition in an amount sufficient to elicit the biological response when the composition is applied to the foliage of the plant at a rate from about 10 to about 1000 liters per hectare (I/ha); and said amine compound(s) being present in the composition in an amount such that the mole ratio of protonatable amino groups in such compound(s) to the exogenous chemical substance is abount 0.05:1 to about 2:1; to form a neutralized composition containing amphiphilic salt(s) of the exogenous chemical substance with said amine compound(s); and (2) a conditioning step wherein agitation of the neutralized composition is continuted until supremolecular aggregates comprising said amphipilic salt(s) are colloidally dispersed in the liquid medium.

35. The process of claim 34 wherein each R group that is an interrupted $C_{6-22}$ hydrocarbyl or acyl chain is interrupted by one or a plurality of functional linkages independently selected from ether, thioether, sulfoxide and thioester linkages.

36. The process of claim 34 wherein the neutralizing step further comprises introducing to the liquid medium, with agitation, a second molar amount $X^2$ of the exogenous chemical substance in the form of one or more salt(s) other than an amphiphilic salt formed by neutralizing the exogenous chemical substance with an amine compound of formula (I), and wherein a zero or third molar amount $X^3$ of the exogenous chemical substance is present in an acid form and is not neutralized; $X^1$ as a fraction of $(X^1+X^2+X^3)$ being about 0.05 to 1.

37. The process of claim 34 wherein the liquid medium is water.

38. The process of claim 34 wherein the anionic exogenous chemical substance is N-phosphonomethylglycine.

39. The process of claim 38 wherein each R group that is an interrupted $C_{6-22}$ hydrocarbyl or acyl chain is interrupted by one or a plurality of functional linkages independently selected from ether, thioether, sulfoxide and thisester linkages.

40. A process for making a liquid concentrate composition suitable for dilution in water to form a plant treatment composition, comprising (1) preparing a first concentrated aqueous solution or dispersion of a water-soluble salt of an anionic exogenous chemical substance, said water-soluble salt having cationic counterions of molecular weight lower that about 100; (2) preparing a second concentrated aqueous solution or dispersion of a salt of an amine compound having a number n of protonatable amino groups, n being at least 1, and having the formula (I)

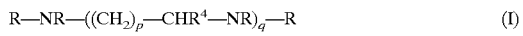

$$R\text{—}NR\text{—}((CH_2)_p\text{—}CHR^4\text{—}NR)_q\text{—}R \qquad (I)$$

wherein q is an integer of 0 to 9, each p is independently an integer of 1 to 5, each $R^4$ group is independently hydrogen or a $C_{1-5}$ alkyl group, and R groups are independently selected from hydrogen, $C_{1-5}$ hydrocarbyl groups and linear or branched, saturated or unsaturated $C_{6-22}$ hydrocarbyl or acyl chains that are (a) unsubstituted or substituted at one or a plurality of carbon atoms with a functional group independently selected from hydroxyl, carboxy, carbamyl, mercapto and cyano groups and (b) uninterrupted or interrupted by one or a plurality of functional linkages independently selected from ether, thioether, sulfoxide, ester, thioester and amide linkages, and terminated by an uninterrupted hydrocarbyl segment having at least 6 carbon atoms; with the proviso that one to three R groups are such $C_{6-22}$ hydrocarbyl or acyl chains, of which at least one is so substituted and/or interrupted; and (3) mixing the first and second concentrated solution or dispersion in such relative amounts as to provide a mole ratio of protonatable amino groups in said amine compound to exogenous chemical substance of about 0.05:1 to about 2:1, said exogenous chemical substance being present in the composition in an amount sufficient to elicit the biological response when the composition is applied to the foliage of the plant at a rate from about 10 to about 1000 liters per hectare (l/ha).

41. The process of claim 40 wherein each R group that is an interrupted $C_{6-22}$ hydrocarbyl or acyl chain is interrupted by one or a plurality of functional linkages independently selected from ether, thioether, sulfoxide and thioether linkages.

42. The process of claim 40 wherein the anionic exogenous chemical substance is N-phosphonomethylglycine.

43. The process of claim 42 wherein each R group that is an interrupted $C_{6-22}$ hydrocarbyl or acyl chain is interrupted by one or a plurality of functional linkages independently selected from ether, thioether, sulfoxide and thioester linkages.

44. A liquid concentrate composition of an anionic exogenous chemical substance prepared by the process of claim 34.

45. The composition of claim 44 wherein each R group that is an interrupted $C_{6-22}$ hydrocarbyl or acyl chain is interrupted by one or a plurality of functional linkages independently selected from ether, thioether, sulfoxide and thioester linkages.

46. The composition of claim 45 wherein the anionic exogenous chemical substance is N-phosphonomethylglycine.

47. A liquid concentrate composition of an anionic exogenous chemical substance prepared by the process of claim 40.

48. The composition of claim 45 wherein the anionic exogenous chemical substance is N-phosphonomethylglycine.

49. The composition of claim 48 wherein the anionic exogenous chemical substance is N-phosphonomethylglycine.

* * * * *

UNITED STATES PATENT AND TRADEMARK OFFICE
CERTIFICATE OF CORRECTION

PATENT NO. : 6,500,783 B1
DATED : December 31, 2002
INVENTOR(S) : Bryson et al.

It is certified that error appears in the above-identified patent and that said Letters Patent is hereby corrected as shown below:

Column 12,
Line 47, please delete "R" and insert therefor -- $R^1$ --.

Column 14,
Lines 57-58, please delete "diethylenetriamine" and insert therefor
-- dibutylenetriamine --.

Column 17,
Line 44, please delete "(VII)" and insert therefor -- (VIII) --.

Column 18,
Line 30, please delete "$x^2$" and insert therefor -- $X^2$ --.

Column 24,
Line 5, please delete "$C_{12-19}$" and insert therefor -- $C_{12-18}$ --.

Column 26,
Line 26, please delete "$[GT^-]_n[A^{n+}]$," and insert therefor -- $[GH^-]_n[A^{n+}]$, --.
Line 41, please delete "$[G^{2-}][B^{n+}]_2$," and insert therefor -- $[G^{2-}][B^+]_2$, --.
Line 48, please delete "$[B^{n+}]$" and insert therefor -- $[B^+]$ --.

Column 28,
Line 48, please delete "multiforum" and insert therefor -- multiflorum --.

Column 35,
Line 48, please delete "Example 9: C14O3-TDA" and insert therefor -- Example 9: C14OC3-TDA --.

Column 37,
Line 44, please delete entire claim 16 and insert therefor
-- A plant treatment composition for application to foliage of a plant to elicit a biological response, comprising an agronomically acceptable liquid carrier, wherein are dissolved or dispersed an anionic exogenous chemical substance and one or more amine compound(s) each the formula

UNITED STATES PATENT AND TRADEMARK OFFICE
CERTIFICATE OF CORRECTION

PATENT NO. : 6,500,783 B1
DATED : December 31, 2002
INVENTOR(S) : Bryson et al.

It is certified that error appears in the above-identified patent and that said Letters Patent is hereby corrected as shown below:

Column 37 (cont'd), $$N(R)_3$$

wherein two R groups are independently hydrogen or $C_{1-5}$ alkyl groups, and one R group is a $C_{6-22}$ hydrocarbyl chain, substituted at one or a plurality of carbon atoms with a functional group Independently selected from hydroxyl, carboxy, carbamyl, mercapto and cyano groups and/or Interrupted by one or a plurality of functional linkages independently selected from ether, thioether, sulfoxide, ester and thioester linkages and terminated by an uninterrupted hydrocarbyl segment having at least 6 carbon atoms; said exogenous chemical substance being present in the composition in an amount sufficient to elicit the biological response when the composition is applied to the foliage of the plant at a rate from about 10 to about 1000 liters per hectare (l/ha); and said amine compound(s) being present in the composition in an amount such that the mole ratio of protonatable amino groups in such compound(s) to the exogenous chemical substance is about 0.05:1 to about 2:1.--.

Column 37,
Line 58, please delete "supermolecular" and insert therefor -- supramolecular --.

Column 38,
Line 28, please delete "interger" and insert therefor -- integer --.
Line 30, please delete "or a $C_{1-5}$ hydrocarbyl groups" and insert therefor -- or a $C_{1-5}$ alkyl group, and R groups are independently selected from hydrogen, $C_{1-5}$ hydrocarbyl groups --.
Line 47, please delete "(I/ha)" and insert therefor -- (1/ha) --.

Column 39,
Line 16, please delete "of which at least one substituted at one or am plurality of" and insert therefor -- of which at least one is sibstituted at one or a plurality of --.
Line 22, please delete "hydrocrabyl" and insert therefor -- hydrocarbyl --.
Lines 24 and 56, please delete "beig" and insert therefor -- being --.
Lines 28 and 60, please delete "(I/ha)" and insert therefor -- (1/ha) --.
Line 48, please delete "hydrogen or a $C_{1-5}$" and insert therefor -- hydrogen or $C_{1-5}$ --.
Line 49, please delete "one R groups" and insert therefor -- one R group --.
Line 53, please delete "functional linkages and" and insert therefor -- functional linkages independently selected from ether, thioether, sulfoxide, ester and thioester linkages and --.
Line 54, please delete "hydrocrabyl" and insert therefor -- hydrocarbyl --.

UNITED STATES PATENT AND TRADEMARK OFFICE
CERTIFICATE OF CORRECTION

PATENT NO. : 6,500,783 B1
DATED : December 31, 2002
INVENTOR(S) : Bryson et al.

It is certified that error appears in the above-identified patent and that said Letters Patent is hereby corrected as shown below:

Column 40,
Line 44, please delete "interger" and insert therefor -- integer --.
Line 45, please delete "or a $C_{1-5}$ hydrocarbyl groups" and insert therefor -- or a $C_{1-5}$ alkyl group, and R groups are independently selected from hydrogen, $C_{1-5}$ hydrocarbyl groups --.
Line 52, please delete "ether, thioether, sulfoxide, and thioester linkages," and insert Therefor -- ether, thioether, sulfoxide, ester, thioester and amide linkages, --.
Line 58, please delete "N-phosphonomethylglycine or a salt thereof and being"
Line 62, please delete "(I/ha)" and insert therefor -- (1/ha) --.

Column 41,
Lines 2-3, please delete "continuted until supremolecular" and insert therefor -- continued until supramolecular --.
Line 4, please delete "amphipilic" and insert therefor -- amphiphilic --.
Line 28, please delete "ether, thioether, sulfoxide and thisester" and insert therefor -- ether, thioether, sulfoxide and thioester --.
Line 36, please delete "that about 100;" and insert therefor -- than about 100; --.

Column 42,
Line 20, please delete "ether, thioether, sulfoxide and thioether" and insert therefor -- ether, thioether, sulfoxide and thioester --.
Please delete claim 48 and insert therefor -- The composition of claim 47 wherein each R group that is an interrupted $C_{6-22}$ hydrocarbyl or acyl chain is interrupted by one or a plurality of functional linkages independently selected from ether, thioether, sulfoxide and thioester linkages. --.

Signed and Sealed this

Ninth Day of March, 2004

JON W. DUDAS
*Acting Director of the United States Patent and Trademark Office*